United States Patent
Sims et al.

(10) Patent No.: US 6,521,740 B1
(45) Date of Patent: *Feb. 18, 2003

(54) TYPE II INTERLEUKIN-1 RECEPTORS

(75) Inventors: John E. Sims, Seattle, WA (US); David J. Cosman, Bainbridge Island, WA (US); Stephen D. Lupton, Seattle, WA (US); Bruce A. Mosley, Seattle, WA (US); Steven K. Dower, Redmond, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/441,893

(22) Filed: May 16, 1995

Related U.S. Application Data

(63) Continuation of application No. 08/242,211, filed on May 13, 1994, now Pat. No. 5,464,937, which is a division of application No. 08/091,519, filed on Jul. 12, 1993, now Pat. No. 5,350,683, which is a continuation of application No. 07/701,415, filed on May 16, 1991, now abandoned, which is a continuation-in-part of application No. 07/627,071, filed on Dec. 13, 1990, now abandoned, which is a continuation-in-part of application No. 07/573,576, filed on Aug. 24, 1990, now abandoned, which is a continuation-in-part of application No. 07/534,193, filed on Jun. 5, 1990, now abandoned.

(51) Int. Cl.$^7$ ................. C07K 14/705; C12N 15/12
(52) U.S. Cl. ................. 530/350; 435/69.1; 536/23.5
(58) Field of Search ................. 530/350; 435/69.1; 536/23.5

(56) References Cited

U.S. PATENT DOCUMENTS 4,675,285 A   6/1987   Clark et al. .................... 435/6

OTHER PUBLICATIONS

Dower et al., *Nature (London)* 324:263 (1986).
Sims et al., *Science* 241: 585 (1988).
Sims et al., *Proc. Natl. Acad. Sci. USA* 86: 8946 (1989).
Matsushima et al., *J. Immunol.* 136: 4496 (1986).
Horuk et al., *J. Biol. Chem.* 262:16275 (1987).
Rhyne et al., *Clin. Immunol. and Immunopathol.* 48: 354 (1988).
Tanaka et al., *J. Immunol.* 142: 167 (1989).
Bomsztyk et al., *J. Biol. Chem.* 264: 6052 (1989).
Scapigliati et al., *FEBS Letters* 243: 394 (1989).
Bensimon et al., *J. Immunol.* 142:2290 (1989).
Bensimon et al., *J. Immunol.* 143:1168 (1989).
Bomsztyk et al., *Proc. Natl. Acad. Sci. USA* 86: 8034 (1989).
Chizzonite et al., *Proc. Natl. Acad. Sci. USA* 86: 8029 (1989).
Mizuno et al., *FEBS Letters* 257: 27 (1989).
Savage et al., *Cytokine* 1: 23 (1989).
Horuk et al., *Biochem. J.* 260: 657 (1989).
Solari, *Cytokine* 2: 21 (1990).
Eastgate et al., *FEBS Letters* 260: 213 (1990).
Benjamin et al., *Blood* 75: 2017 (1990).
Okayama and Berg, *Mol. Cell. Biol.* 2:161 (1982).
Okayama and Berg, *Mol. Cell. Biol.* 3:280 (1983).
Aruffo and Seed, *Proc. Natl. Acad. Sci. USA* 84:8573 (1987).
Yamasaki et al., *Science* 241:825 (1988).
Yates et al., *Proc. Natl. Acad. Sci. USA* 81: 3806, (1984).
Lupton et al., *Mol. Cell. Biol.* 5: 2533 (1985).
Pfitzner et al., *J. Virol.* 61: 2902 (1987).
Klemenz et al., *Proc. Natl. Acad. Sci. USA* 86: 5708 (1989).
Tominaga, *FEBS Letters* 258: 301 (1989).
Fearon et al., *Science* 247: 49 (1990).
Gearing et al., *EMBO* 8:3367 (1989).
Giri et al. *J. Biol. Chem.* 265:17416–17419 (1990).
Smith et al. *Science* 238:1704–07 (1987).
Sims et al. *Proc. Natl. Acad. Sci. USA* 90:6155–6159 (1993).
Colotta et al. *Science* 261:472–475 (1993).
Leonard et al., *Nature* 311:676 (1984).
Belyavsky et al., *Nucl. Acids Res.* 17:2919 (1989).
Treiger et al., *J. Immunol.* 136:4099 (1986).

*Primary Examiner*—John Ulm
(74) *Attorney, Agent, or Firm*—Janis C. Henry; Patricia Anne Perkins

(57) ABSTRACT

Type II IL-1 receptor (type II IL-1R) proteins, DNAs and expression vectors encoding type II IL-1R, and processes for producing type II IL-1R as products of recombinant cell culture, are disclosed.

4 Claims, 4 Drawing Sheets

```
Vaccinia       ...KSI..VIFLS..DYFYSSFVQ

Comparison of Natural and Recombinant IL-1 Receptors by Crosslinking

TYPE II INTERLEUKIN-1 RECEPTORS

CROSS-REFERENCE TO RELATED APPLICATION

This application is a continuation of U.S. Ser. No. 08/242,211, filed May 13, 1994 now U.S. Pat. No. 5,464,937, which was a divisional of U.S. Ser. No. 08/091,519, filed Jul. 12, 1993, issued as U.S. Pat. No. 5,350,683 on Sep. 27, 1994, which is a continuation of U.S. application Ser. No. 07/701,415, filed May 16, 1991, now abandoned, which is a continuation-in-part of U.S. application Ser. No. 07/627,071, filed Dec. 13, 1990, now abandoned, which is a continuation-in-part of U.S. application Ser. No. 07/573,576, filed Aug. 24, 1990, now abandoned, which is a continuation-in-part of U.S. application Ser. No. 07/534,193, filed Jun. 5, 1990, now abandoned.

BACKGROUND OF THE INVENTION

The present invention relates generally to cytokine receptors, and more specifically, to Type II (B Cell) Interleukin-1 receptors.

Interleukin-1α (IL-1α) and Interleukin-1β (IL-1β) are distantly related polypeptide hormones which play a central role in the regulation of immune and inflammatory responses. These two proteins act on a variety of cell types and have multiple biological activities. The diversity of biological activity ascribed to IL-1α and IL-1β is mediated by specific plasma membrane receptors which bind both IL-1α and IL-1β. Due to the wide range of biological activities mediated by IL-1α and IL-1β it was originally believed that the IL-1 receptors should be highly conserved in a variety of species and expressed on a large variety of cells.

Structural chracterization by ligand affinity cross-linking techniques has demonstrated that, despite their significant divergence in sequence, IL-1α and IL-1β bind to the same cell surface receptor molecule on T cells and fibroblasts (Dower et al., *Nature (London)* 324:266, 1986; Bird et al., *Nature (London)* 324:263, 1986; Dower et al., *Proc. Natl. Acad. Sci. USA* 83:1060, 1986). The IL-1 receptor on murine and human T cells has been identified by cDNA expression cloning and N-terminal sequence analysis as an integral membrane glycoprotein that binds IL-1α and IL-1β and has a molecular weight of 80,000 kDa (Sims et al., *Science* 241:585, 1988; Sims et al., *Proc. Natl. Acad. Sci. USA* 86:8946, 1989).

Subsequent affinity cross-linking studies indicate that IL-1 receptors on the Epstein Barr virus (EBV)-transformed human B cell lines VDS-O and 3B6, the EBV-positive Burkitt's lymphoma cell line Raji, and the murine pre-B cell line 70Z/3, have a molecular weight of 60,000 to 68,000 kDa (Matsushima et al., *J. Immunol.* 136:4496, 1986; Bensimon et al., *J. Immunol.* 142:2290, 1989; Bensimon et al., *J. Immunol.* 143:1168, 1989; Horuk et al., *J. Biol. Chem.* 262:16275, 1987; Chizzonite et al., *Proc. Natl. Acad. Sci. USA* 86:8029, 1989; Bomsztyk et al., *Proc. Natl. Acad. Sci. USA* 86:8034, 1989). Moreover, comparison of the biochemical properties and kinetic analysis of the IL-1 receptor in the Raji B cell line with EL-4 murine T lymphoma cell line showed that Raji cells had lower binding affinity but much higher receptor density per cell than a subclone of EL-4 T cells (Horuk et al., *J. Biol. Chem.* 262:16275, 1987). Raji cells also failed to internalize IL-1 and demonstrated altered receptor binding affinities with IL-1 analogs. (Horuk et al., *J. Biol. Chem.* 262:16275, 1987). These data suggest that the IL-1 receptors expressed on B cells (referred to herein as type II IL-1 receptors) are different from IL-1 receptors detected on T cells and other cell types (referred to herein as type I IL-1 receptors).

In order to study the structural and biological characteristics of type II IL-1R and the role played by type II IL-1R in the responses of various cell populations to IL-1 stimulation, or to use type II IL-1R effectively in therapy, diagnosis, or assay, homogeneous compositions are needed. Such compositions are theoretically available via purification of receptors expressed by cultured cells, or by cloning and expression of genes encoding the receptors. Prior to the present invention, however, several obstacles prevented these goals from being achieved.

First, no cell lines have previously been known to express high levels of type II IL-1R constitutively and continuously, and cell lines known to express type II IL-1R did so only in low numbers (500 to 2,000 receptors/cell) which impeded efforts to purify receptors in amounts sufficient for obtaining amino acid sequence information or generating monoclonal antibodies. The low numbers of receptors has also precluded any practical translation assay-based method of cloning.

Second, the significant differences in DNA sequence between type I IL-1R and type II IL-1R has precluded cross-hybridization using a murine type IL-1R cDNA (Bomsztyk et al., *Proc. Natl. Acad. Sci. USA* 86:8034, 1989, and Chizzonite et al., *Proc. Natl. Acad. Sci. USA* 86:8029, 1989).

Third, even if a protein composition of sufficient purity could be obtained to permit N-teriminal protein sequencing, the degeneracy of the genetic code may not permit one to define a suitable probe without considerable additional experimentation. Many iterative attempts may be required to define a probe having the requisite specificity to identify a hybridizing sequence in a cDNA library. Although direct expression cloning techniques avoid the need for repetitive screening using different probes of unknown specificity and have been useful in cloning other receptors (e.g., type I IL-1R), they are not sufficiently sensitive to be suitable for using in identifying type II IL-1R clones from cDNA libraries derived from cells expressing low numbers of type II IL-1R.

Thus, efforts to purify the type II IL-1R or to clone or express genes encoding type II IL-1R have been significantly impeded by lack of purified receptor, a suitable source of receptor mRNA, and by a sufficiently sensitive cloning technique.

SUMMARY OF THE INVENTION

The present invention provides isolated type II IL-1R and isolated DNA sequences encoding type II IL-1R, in particular, human type II IL-1R, or analogs thereof. Preferably, such DNA sequences are selected from the group consisting of (a) cDNA clones having a nucleotide sequence derived from the coding region of a native type II IL-1R gene, such as clone 75; (b) DNA sequences capable of hybridization to the cDNA clones of (a) under moderately stringent conditions and which encode biologically active IL-1R molecules; and (c) DNA sequences which are degenerate as a result of the genetic code to the DNA sequences defined in (a) and (b) and which encode biologically active IL-1R molecules. The present invention also provides recombinant expression vectors comprising the DNA sequences defined above, recombinant type II IL-1R molecules produced using the recombinant expression vectors, and processes for producing the recombinant type II IL-1R molecules utilizing the expression vectors.

The present invention also provides substantially homogeneous protein compositions comprising type II IL-1R.

The present invention also provides compositions for use in therapy, diagnosis, assay of type II IL-1R, or in raising antibodies to type II IL-1R, comprising effective quantities of soluble native or recombinant receptor proteins prepared according to the foregoing processes.

These and other aspects of the present invention will become evident upon reference to the following detailed description.

BRIEF DESCRIPTION OF THE DRAWINGS

FIG. 3 compares the amino acid sequences of the human and murine type II IL-1 receptors (as deduced from the cDNA clones) with the amino acid sequences of the human and murine type I IL-1 receptors (Sims eat al., *Proc. Natl. Acad. Sci. USA* 86:8946, 1989; Sims et al., *Science* 241:585, 1988; SEQ ID NOS:16 and 17 respectively) and amino acid sequences of the ST2 cellular gene (Tominaga, *FEBS Lett.* 258:301, 1989; SEQ ID NO:18) and the B15R open reading frame of vaccinia virus (Smith and Chan, *J. Gen. Virology* 72:511, 1991; SEQ ID NO:19). Numbering begins with the initiating methionine. The predicted position of the signal peptide cleavage in each sequences was determined according to the method described by von Heijne, *Nucl. Acids. Res.* 14:4683, 1986, and is indicated by a gap between the putative signal peptide and the main body of the protein. The predicated transmembrane and cytoplasmic regions for the type II IL-1 receptors are shown on the bottom line, and are separated from one another by a gap. Residues conserved in all four IL-1 receptor sequences are presented in white on a black background. Residues conserved in type II receptors that are also found in one of the other sequences are shaded; residues conserved in type I IL-1 receptors that are found in one of the other sequences are boxed. Cysteine residues involved in forming the disulfide bonds characteristic of the immunolgobulin fold are marked with solid dots, while the extra two pairs of cysteines found in the type I IL-1 receptor and in some of the other sequences are indicated by stars. The approximate boundaries of domains 1, 2 and 3 are indicated above the lines. The predicted signal peptide cleavage in the type II IL-1 receptors follow Ala13, resulting in an unusually short signal peptide and an N-terminal extension of 12 (human) or 23 (mouse) amino acids beyond the point corresponding to the mature N-terminus of the human or mouse type I IL-1 receptor. Other less favored but still acceptable sites of cleavage in the murine type II IL-1 receptor are after Thr15 or Pro17. This sequence alignment was made by hand and does not represent an objectively optimized alignment of the sequences. The nucleotide and amino acid sequences of the full length and soluble human and murine type II IL-1 receptor cDNAs are also set forth in the Sequence Listing herein.

DETAILED DESCRIPTION OF THE INVENTION

Definitions

Figure 1:
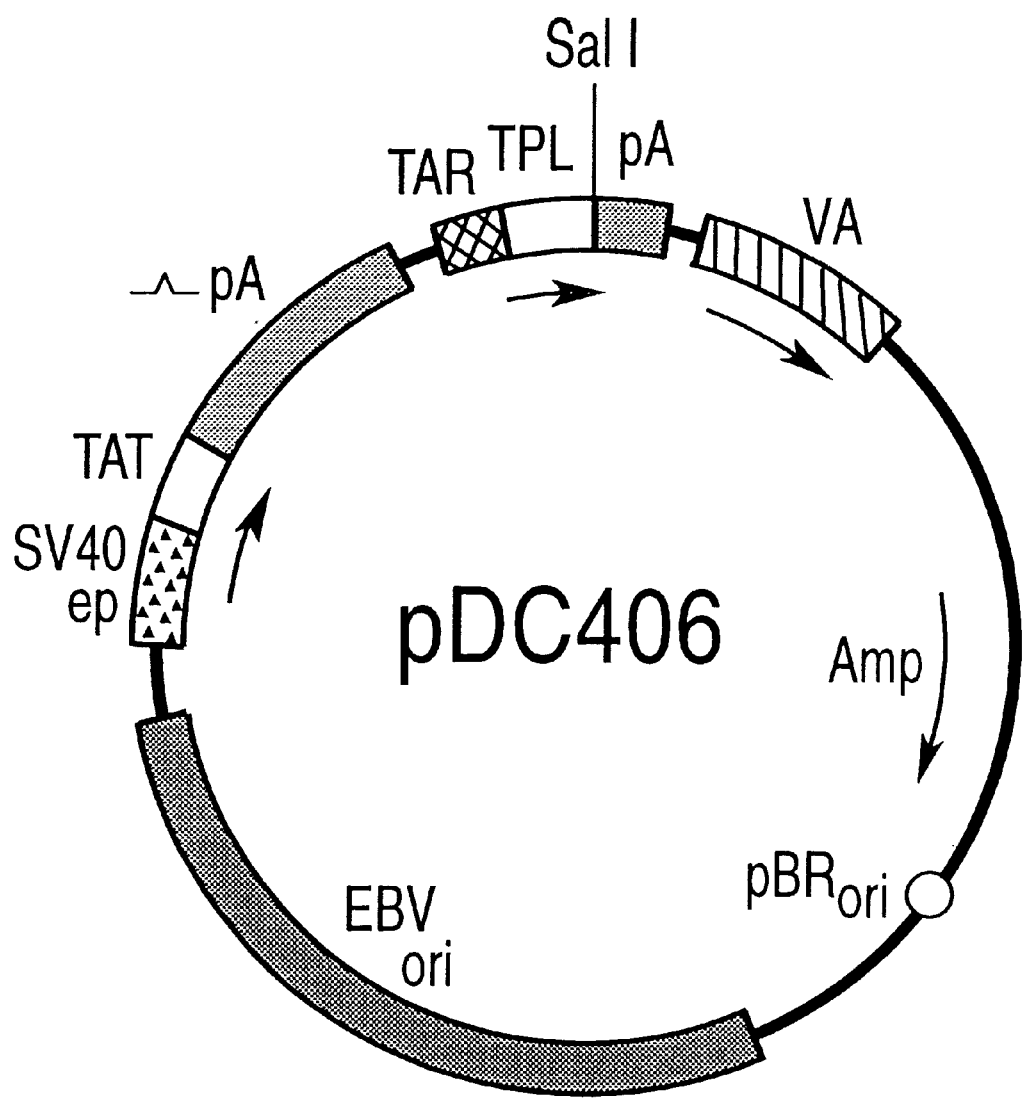
FIG. 1 is a scehmatic diagram of the expression plasmid pDC406. cDNA molecules inserted at the Sal site are transcribed and translated using regulatory elements derived from HIV and adenovirus. pDC406 contains origins of replication derived from SV40, Epstein-Barr virus and pBR322.
Figure 2:
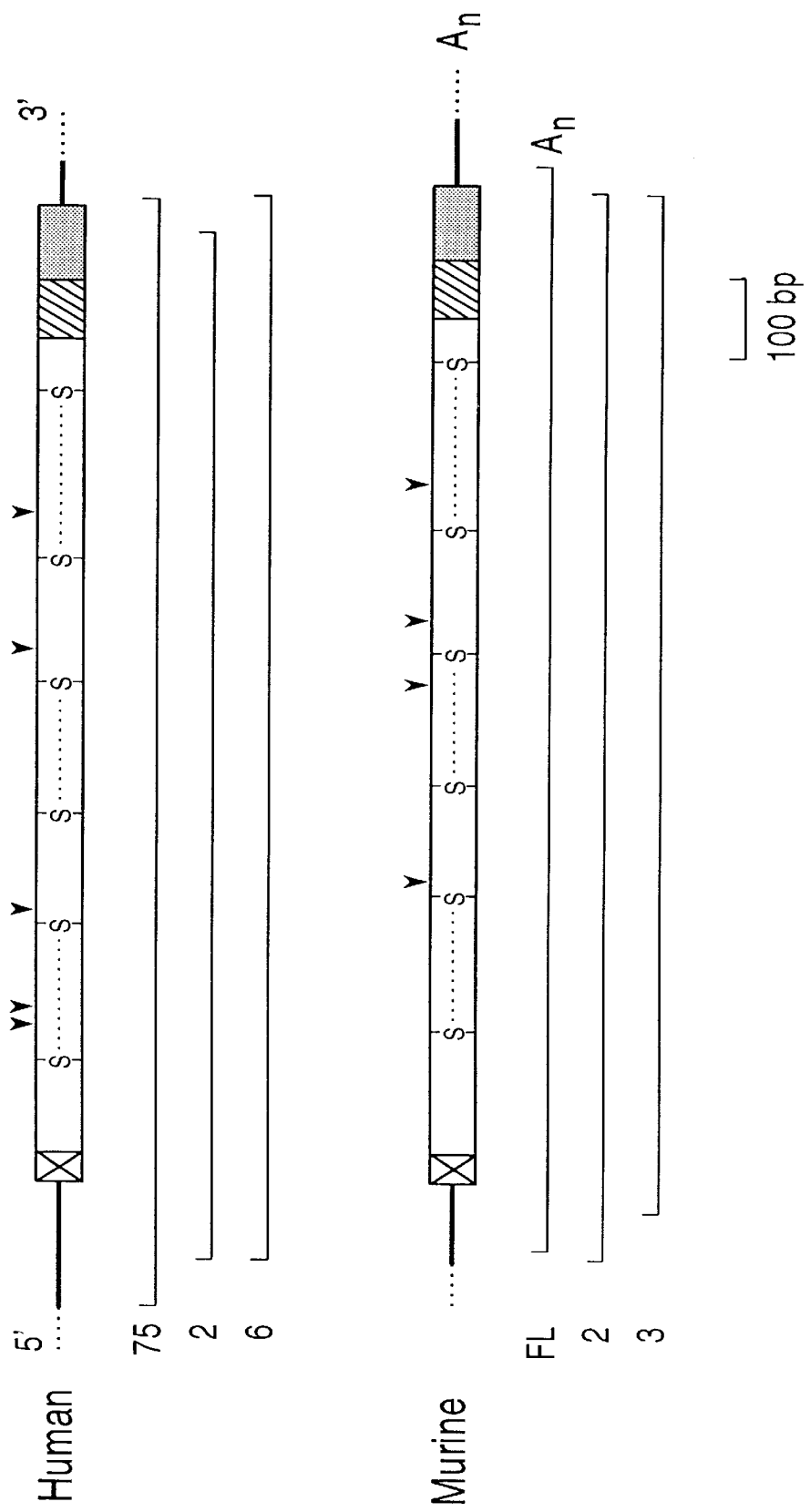
FIG. 2 is a schematic diagram of the human and murine type II IL-1receptors and the various human and murine clones used to determine the sequences. Thin lines represent untranslated regions, while the coding region is depicted by a box. The sections encoding the signal peptide are filled in; the transmembrane regions are cross-hatched; and the cytoplasmic portions are stippled. Potential N-linked glycosylation sites are marked by inverted triangles. The predicted immunoglobulin-like disulfide bonds are also indicated by dashes connecting two sulfide molecules (S-----S).

"IL-1" refers collectively to IL-1α and IL-1β.

"Type II Interleukin-1 receptor" and "type II IL-1R" refer to proteins which are capable of binding Interleukin-1 (IL-1) molecules. The mature full-length human type II IL-1R is a glycoprotein having an apparent molecular weight of approximately 60–68 kDa. Specific examples of type II IL-1R proteins are shown in SEQ ID NO:1 and SEQ ID NO:12. As used herein, the above terms include analogs or subunits of native type II IL-1R proteins with IL-1-binding activity. Specifically included are truncated or soluble forms of type II IL-1R protein, as defined below. In the absence of any species designation, type II IL-1R refers generically to mammalian type II IL-1R, which includes, but is not limited to, human, murine, and bovine type II IL-1R. Similarly, in the absence of any specific designation for deletion mutants, the term type II IL-1R means all forms of type II IL-1R, including mutants and analogs which possess type II IL-1R biological activity. "Interleukin-1 Receptor" or "IL-1R" refers collectively to type I IL-1 receptor and type II IL-1 receptor.

"Soluble type II IL-1R" as used in the context of the present invention refer to proteins, or substantially equivalent analogs, which are substantially similar to all or part of the extracellular region of a native type II IL-1R, and are secreted by the cell but retain the ability to bind IL-1 or inhibit IL-1 signal transduction activity via cell surface bound IL-1R proteins. Soluble type II IL-1R proteins may also include part of the transmembrane region, provided that the soluble type II IL-1R protein is capable of being secreted from the cell. Specific examples of soluble type II IL-1R proteins include proteins having the sequence of amino acids 1–330 or amino acids 1–333 of SEQ ID NO:1 and amino acids 1–342 and amino acids 1–345 of SEQ ID NO:12. Inhibition of IL-1 signal transduction activity can be determined using primary cells or cells lines which express an endogenous IL-1R and which are biologically responsive to IL-1 or which, when transfected with recombinant IL-1R DNAs, are biologically responsive to IL-1. The cells are then contacted with IL-1 and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al.,*J. Exp. Med.* 171:861 (1990); Curtis et al., *Proc. Natl. Acad. Sci. USA* 86:3045 (1989); Prywes et al., *EMBO J.* 5:2179 (1986) and Chou et al., *J. Biol. Chem.* 262:1842 (1987).

The term "isolated" or "purified", as used in the context of this specification to define the purity of type II IL-1 R protein or protein compositions, means that the protein or protein composition is substantially free of other proteins of natural or endogenous origin and contains less than about 1% by mass of protein contaminants residual of production processes. Such compositions, however, can contain other proteins added as stabilizers, carriers, excipients or co-therapeutics. Type II IL-1R is "isolated" if it is detectable as a single protein band in a polyacrylamide gel by silver staining.

The term "substantially similar," when used to define either amino acid or nucleic acid sequences, means that a particular subject sequence, for example, a mutant sequence, varies from a reference sequence by one or more substitutions, deletions, or additions, the net effect of which is to retain biological activity of the type II IL-1R protein as may be determined, for example, in a type II IL-1R binding assays, such as is described in Example 5 below. Alternatively, nucleic acid subunits and analogs are "substantially similar" to the specific DNA sequences disclosed herein if: (a) the DNA sequence is derived from the coding region of SEQ ID NO:1 or SEQ ID NO:12; (b) the DNA sequence is capable of hybridization to DNA sequences of (a) under moderately stringent conditions (25% formamide, 42° C., 2×SSC) or alternatively under more stringent conditions (50% formamide, 50° C., 2×SSC or 50% formamide, 42° C., 2×SSC) and which encode biologically active IL-1R molecules; or DNA sequences which are degenerate as a result of the genetic code to the DNA sequences defined in (a) or (b) and which encode biologically active IL-1R molecules.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., $E.$ $coli,$ will be free of glycan; protein expressed in yeast may have a glycosylation pattern different from that expressed in mammalian cells.

"Biologically active," as used throughout the specification as a characteristic of type II IL-1R, means either that a particular molecule shares sufficient amino acid sequence similarity with SEQ ID NO:2 or SEQ ID NO:13 to be capable of binding detectable quantities of IL-1, preferably at least 0.01 nmoles IL-1 per nanomole type II IL-1R, for example, as a component of a hybrid receptor construct. More preferably, biologically active type II IL-1R within the scope of the present invention is capable of binding greater than 0.1 nanomoles IL-1 per nanomole receptor, and most preferably, greater than 0.5 nanomoles IL-1 per nanomole receptor.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention are assembled from cDNA fragments and short oligonucleotide linkers, or from a series of oligonucleotides, to provide a synthetic gene which is capable of being expressed in a recombinant transcriptional unit.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as $E.$ $coli$ or yeast such as $S.$ $cerevisiae,$ which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of cDNAs Encoding Type II IL-1R

In order to secure a human coding sequence, a DNA sequence encoding human type II IL-1R (see SEQ ID NO:1) was isolated from a cDNA library prepared using standard methods by reverse transcription of polyadenylated RNA isolated from the human B cell lymphoblastoid line CB23, described by Benjamin & Dower, *Blood* 75:2017, 1990. Briefly, the CB23 cell line is an EBV-transformned cord blood (CB) lymphocyte cell line, which was derived using the methods described by Benjamin et al., *Proc. Natl. Acad. Sci. USA* 81:3547, 1984.

The CB23 library was screened by modified direct expression of pooled cDNA fragments in the monkey kidney cell line CV-1/EBNA-1 using a mammalian expression vector (pDC406) that includes regulatory sequences derived from SV40 and human immunodeficiency virus (HIV), and Epstein-Barr virus (EBV). The CV-1/EBNA-1 cell line was derived by transfection of the CV-1 cell line with the gene encoding Epstein-Barr virus nuclear antigen-1 (EBNA-1) and constitutively expresses EBNA-1 driven from the human CMV immediate-early enhancer/promoter. The EBNA-1 gene allows the episomal replication of expression vectors such as pDC406 that contain the EBV origin of replication.

Transfectants expressing biologically active type II IL-1R were initially identified using a modified slide autoradiographic technique, substantially as described by Gearing et al., *EMBO J.* 8:3667, 1989. Briefly, CV-1/EBNA-1 cells were transfected with miniprep DNA in pDC406 from pools of cDNA clones directly on glass slides and cultured for 2–3 days to permit transient expression of type II IL-1R. The slides containing the transfected cells were then incubated with medium containing $^{125}$I-IL-1β, washed to remove unbound labeled IL-1β, fixed with glutaraldehyde, and dipped in liquid photographic emulsion and exposed in the dark. After developing the slides, they were individually examined with a microscope and positive cells expressing type II IL-1R were identified by the presence of autoradiographic silver grains against a light background.

Using this approach, approximately 250,000 cDNAs were screened in pools of approximately 3,000 cDNAs using the slide autoradiographic method until assay of one transfectant pool showed multiple cells clearly positive for IL-1β binding. This pool was then partitioned into pools of 500 and again screened by slide autoradiography and a positive pool was identified. This pool was further partitioned into pools of 75 and screened by plate binding assays analyzed by quantitation of bound $^{125}$I-IL-1β. The cells were scraped off and counted to determine which pool of 75 was positive. Individual colonies from this pool of 75 were screened until a single clone (clone 75) was identified which directed synthesis of a surface protein with detectable IL-1β binding activity. This clone was isolated, and its insert was sequenced to determine the sequence of the human type II IL-1R cDNA clone 75 (SEQ ID NO:1). The pDC406 cloning vector containing the human type II IL-1R cDNA, designated pHuTYPE II IL-1R 75, was deposited with the American Type Culture Collection, Rockville, Md., USA (ATCC) on Jun. 5, 1990 under accession number 68337. The deposit was made under the conditions of the Budapest Treaty.

A probe may be constructed from the human sequence and used to screen various other mammalian cDNA libraries. cDNA clones which hybridized to the human probe are then isolated and sequenced.

Like most mammalian genes, mammalian type II IL-1R is presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Proteins and Analogs

The present invention provides isolated recombinant mammalian type II IL-1R polypeptides. Isolated type II IL-1R polypeptides of this invention are substantially free of other contaminating materials of natural or endogenous origin and contain less than about 1% by mass of protein contaminants residual of production processes. The native human type II IL-1R molecules are recovered from cell lysates as glycoproteins having an apparent molecular weight by SDS-PAGE of about 60–68 kilodaltons (kDa). The type II IL-1R polypeptides of this invention are optionally without associated native-pattern glycosylation.

Mammalian type II IL-1R of the present invention includes, by way of example, primate, human, murine, canine, feline, bovine, ovine, equine, caprine and porcine type II IL-1R. Mammalian type II IL-1R can be obtained by cross species hybridization, using a single stranded cDNA derived from the human type II IL-1R DNA sequence, for example, clone 75, as a hybridization probe to isolate type II IL-1R cDNAs from mammalian cDNA libraries. DNA sequences which encode IL-1R-II, possibly in the form of alternate splicing arrangements, can be isolated from the following cells and tissues: B lymphoblastoid lines (such as CB23, CB33, Raji, RPMI1788, ARH77), resting and especially activated peripheral blood T cells, monocytes, the monocytic cell line THP1, neutrophils, bone marrow, placenta, endothelial cells, keratinocytes (especially activated), and HepG2 cells.

Derivatives of type II IL-1R within the scope of the invention also include various structural forms of the primary protein which retain biological activity. Due to the presence of ionizable amino and carboxyl groups, for example, a type II IL-1R protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to type II IL-1R amino acid side chains or at the N- or C-termini. Other derivatives of type II IL-1R within the scope of this invention include covalent or aggregative conjugates of type II IL-1R or its fragments with other proteins or polypeptides, such as by synthesis in recombinant culture as N-terminal or C-terminal fusions. For example, the conjugated peptide may be a a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). Type II IL1R protein fusions can comprise peptides added to facilitate purification or identification of Type II IL-1R (e.g., poly-His). The amino acid sequence of type II IL-1R can also be linked to the peptide Asp-Tyr-Lys-Asp-Asp-Asp-Asp-Lys (DYKDDDDK; SEQ ID NO:15) (Hopp et al., *Bio/Technology* 6:1204,1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*.

Type II IL-1R derivatives may also be used as immunogens, reagents in receptor-based immunoassays, or as binding agents for affinity purification procedures of IL-1 or other binding ligands. type II IL-1R derivatives may also be obtained by cross-linking agents, such as M-maleimidobenzoyl succinimide ester and N-hydroxysuccinimide, at cysteine and lysine residues. Type II IL-1R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, type II IL-1R may be used to selectively bind (for purposes of assay or purification) anti-type II IL-1R antibodies or IL-1.

The present invention also includes type II IL-1R with or without associated native-pattern glycosylation. Type II IL-1R expressed in yeast or mammalian expression systems, e.g., COS-7 cells, may be similar or slightly different in molecular weight and glycosylation pattern than the native molecules, depending upon the expression system. Expression of type II IL-1R DNAs in bacteria such as *E. coli* provides non-glycosylated molecules. Functional mutant analogs of mammalian type II IL-1R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Examples of N-glycosylation sites in human type II IL-1R are amino acids 66–68, 72–74, 112–114, 219–221, and 277–279 in SEQ ID NO:1. Such sites can be eliminated by substituting another amino acid for Asn or for residue Z, deleting Asn or Z, or inserting a non-Z amino acid between $A_1$ and Z, or an amino acid other than Asn between Asn and $A_1$.

Type II IL-1R derivatives may also be obtained by mutations of type II IL-1R or its subunits. A type II IL-1R mutant, as referred to herein, is a polypeptide homologous to type II IL-1R but which has an amino acid sequence different from native type II IL-1R because of a deletion, insertion or substitution.

Bioequivalent analogs of type II IL-1R proteins may be constructed by, for example, making various substitutions of residues or sequences or deleting terminal or internal residues or sequences not needed for biological activity. For example, cysteine residues can be deleted or replaced with other amino acids to prevent formation of unnecessary or incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. Substantially similar polypeptide sequences, as defined above, generally comprise a like number of amino acids sequences, although C-terminal truncations for the purpose of constructing soluble type II IL-1Rs will contain fewer amino acid sequences. In order to preserve the biological activity of type II IL-1Rs, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian type II IL-1Rs is suggestive of additional conservative substitutions that may be made without altering the essential biological characteristics of type I IL-1R.

Subunits of type II IL-1R may be constructed by deleting terminal or internal residues or sequences. The present invention contemplates, for example, C terminal deletions which result in soluble type II IL-1R constructs corresponding to all or part of the extracellular region of type II IL-1R. The resulting protein preferably retains its ability to bind IL-1. Particularly preferred sequences include those in which the transmembrane region and intracellular domain of type II IL-1R are deleted or substituted with hydrophilic residues to facilitate secretion of the receptor into the cell culture medium. Soluble type II IL-1R proteins may also include part of the transmembrane region, provided that the soluble type II IL-1R protein is capable of being secreted from the cell. For example, soluble human type II IL-1R may comprise the sequence of amino acids 1–333 or amino acids 1–330 of SEQ ID NO:1 and amino acids 1–345 and amino acids 1–342 of SEQ ID NO:12. Alternatively, soluble type II IL-1R proteins may be derived by deleting the C-terminal region of a type II IL-1R within the extracellular region which are not necessary for IL-1 binding. For example, C-terminal deletions may be made to proteins having the sequence of SEQ ID NO:1 and SEQ ID NO:12 following amino acids 313 and 325, respectively. These amino acids are cysteines which are believed to be necessary to maintain the tertiary structure of the type II IL-1R molecule and permit binding of the type II IL-1R molecule to IL-1. Soluble type II IL-1R constructs are constructed by deleting the 3'-terminal region of a DNA encoding the type II IL-1R and then inserting and expressing the DNA in appropriate expression vectors. Exemplary methods of constructing such soluble proteins are described in Examples 2 and 4. The resulting soluble type II IL-1R proteins are then assayed for the ability to bind IL-1, as described in Example 5. Both the DNA sequences encoding such soluble type II IL-1Rs and the biologically active soluble type II IL-1R proteins resulting from such constructions are contemplated to be within the scope of the present invention.

Mutations in nucleotide sequences constructed for expression of analog type I IL-1R must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed type II IL-1R mutants screened for the desired activity.

Not all mutations in the nucleotide sequence which encodes type II IL-1R will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); and U.S. Pat. Nos. 4,518,584 and 4,737,462 disclose suitable techniques, and are incorporated by reference herein.

Both monovalent forms and polyvalent forms of type II IL-1R are useful in the compositions and methods of this invention. Polyvalent forms possess multiple type II IL-1R binding sites for IL-1 ligand. For example, a bivalent soluble type II IL-1R may consist of two tandem repeats of the extracellular region of type II IL-1R, separated by a linker region. Alternate polyvalent forms may also be constructed, for example, by chemically coupling type II IL-1R to any clinically acceptable carrier molecule, a polymer selected from the group consisting of Ficoll, polyethylene glycol or dextran using conventional coupling techniques. Alternatively, type II IL-1R may be chemically coupled to biotin, and the biotin-type II IL-1R conjugate then allowed to bind to avidin, resulting in tetravalent avidin/biotin/type II IL-1R molecules. Type II IL-1R may also be covalently coupled to dinitrophenol (DNP) or trinitrophenol (TNP) and the resulting conjugate precipitated with anti-DNP or anti-TNP-IgM, to form decameric conjugates with a valency of 10 for type II IL-1R binding sites.

A recombinant chimeric antibody molecule may also be produced having type II IL-1R sequences substituted for the variable domains of either or both of the immunoglubulin molecule heavy and light chains and having unmodified constant region domains. For example, chimeric type II IL-1R/IgGI may be produced from two chimeric genes—a type II IL-1R/human κ light chain chimera (type II IL-1R/$C_\kappa$) and a type II EL-1R/human γ1 heavy chain chimera (type II IL-1R/$C_{\gamma-1}$). Following transcription and translation of the two chimeric genes, the gene products assemble into a single chimeric antibody molecule having type II IL-1R displayed bivalently. Such polyvalent forms of type II IL-1R may have enhanced binding affinity for IL-1 ligand. Additional details relating to the construction of such chimeric antibody molecules are disclosed in WO 89/09622 and EP 315062.

Expression of Recombinant Type II IL-1R

The present invention provides recombinant expression vectors to amplify or express DNA encoding type II IL-1R. Recombinant expression vectors are replicable DNA constructs which have synthetic or cDNA-derived DNA fragments encoding mammalian type II IL-1R or bioequivalent analogs operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

DNA sequences encoding mammalian type II IL-1Rs which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to clone 75 under moderately stringent conditions (50° C., 2×SSC) and other sequences hybridizing or degenerate to those which encode biologically active type II IL-1R polypeptides.

Recombinant type II IL-1R DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells which have been transformed or transfected with type II IL-1R vectors constructed using recombinant DNA techniques. Transformed host cells ordinarily express type II IL-1R, but host cells transformed for purposes of cloning or amplifying type II IL-1R DNA do not need to express type II IL-1R. Expressed type II IL-1R will be deposited in the cell membrane or secreted into the culture supernatant, depending on the type II IL-1R DNA selected. Suitable host cells. for expression of mammalian type II IL-1R include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce mammalian type II IL-1R using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of type II IL-1R that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium,* and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Recombinant type II IL-1R proteins may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding type II IL-1R, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* TRP1 or URA3 gene, which provides a selection marker for a mutant strain of yeast lacking the ability to grow in tryptophan, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pUC18 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kuran et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil or URA+ tranformants in medium consisting of 0.67% YNB, with amino acids and bases as described by Sherman et al., *Laboratory Course Manual for Methods in Yeast Genetics*, Cold Spring Harbor Laboratory, Cold Spring Harbor, N.Y., 1986.

Host strains transformed by vectors comprising the ADH2 promoter may be grown for expression in a rich medium consisting of 1% yeast extract, 2% peptone, and 1% or 4% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express recombinant protein. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind 3 site toward the Bgl1 site located in the viral origin of replication is included. Further, mammalian genomic type II IL-1R promoter, control and/or signal sequences may be utilized, provided such control sequences are compatible with the host cell chosen. Additional details regarding the use of a mammalian high expression vector to produce a recombinant mammalian type II IL-1R are provided in Examples 2 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

In preferred aspects of the present invention, recombinant expression vectors comprising type II IL-1R cDNAs are stably integrated into a host cell's DNA. Elevated levels of expression product is achieved by selecting for cell lines having amplified numbers of vector DNA. Cell lines having amplified numbers of vector DNA are selected, for example, by transforming a host cell with a vector comprising a DNA sequence which encodes an enzyme which is inhibited by a known drug. The vector may also comprise a DNA sequence which encodes a desired protein. Alternatively, the host cell may be co-transformed with a second vector which comprises the DNA sequence which encodes the desired protein. The transformed or co-transformed host cells are then cultured in increasing concentrations of the known drug, thereby selecting for drug-resistant cells. Such drug-resistant cells survive in increased concentrations of the toxic drug by over-production of the enzyme which is inhibited by the drug, frequently as a result of amplification of the gene encoding the enzyme. Where drug resistance is caused by an increase in the copy number of the vector DNA encoding the inhibitable enzyme, there is a concomitant co-amplification of the vector DNA encoding the desired protein (e.g., type II IL-1R) in the host cell's DNA.

A preferred system for such co-amplification uses the gene for dihydrofolate reductase (DHFR), which can be inhibited by the drug methotrexate (MTX). To achieve co-amplification, a host cell which lacks an active gene encoding DHFR is either transformed with a vector which comprises DNA sequence encoding DHFR and a desired protein, or is co-transformed with a vector comprising a DNA sequence encoding DHFR and a vector comprising a DNA sequence encoding the desired protein. The transformed or co-transformed host cells are cultured in media containing increasing levels of MTX, and those cells lines which survive are selected.

A particularly preferred co-amplification system uses the gene for glutamine synthetase (GS), which is responsible for the synthesis of glutamine from glutamate and ammonia using the hydrolysis of ATP to ADP and phosphate to drive the reaction. GS is subject to inhibition by a variety of inhibitors, for example methionine sulphoximine (MSX). Thus, type II IL-1R can be expressed in high concentrations by co-amplifying cells transformed with a vector comprising the DNA sequence for GS and a desired protein, or co-transformed with a vector comprising a DNA sequence encoding GS and a vector comprising a DNA sequence encoding the desired protein, culturing the host cells in media containing increasing levels of MSX and selecting for surviving cells. The GS co-amplification system, appropriate recombinant expression vectors and cells lines, are described in the following PCT applications: WO 87/04462, WO 89/01036, WO 89/10404 and WO 86/05807.

Recombinant proteins are preferably expressed by co-amplification of DHFR or GS in a mammalian host cell, such as Chinese Hamster Ovary (CHO) cells, or alternatively in a murine myeloma cell line, such as SP2/0-Ag14 or NSO or a rat myeloma cell line, such as YB2/3.0-Ag20, disclosed in PCT applications WO/89/10404 and WO 86/05807.

A preferred eukaryotic vector for expression of type II IL-1R DNA is disclosed below in Example 2. This vector, referred to as pDC406, was derived from the mammalian high expression vector pDC201 and contains regulatory sequences from SV40, HIV and EBV.

Purification of Recombinant Type II IL-1R

Purified mammalian type II IL-1Rs or analogs are prepared by culturing suitable host/vector systems to express the recombinant translation products of the DNAs of the present invention, which are then purified from culture media or cell extracts.

For example, supernatants from systems which secrete recombinant soluble type II IL-1R protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an IL-1 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a type II IL-1R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian type II IL-1R can be disrupted by any convenient method, including freeze-thaw cycling, sonication, mechanical disruption, or use of cell lysing agents.

Fermentation of yeast which express soluble mammalian type II IL-1R as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Human type II IL-1R synthesized in recombinant culture is characterized by the presence of non-human cell components, including proteins, in amounts and of a character which depend upon the purification steps taken to recover human type II IL-1R from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of type II IL-1R free of proteins which may be normally associated with type II IL-1R as it is found in nature in its species of origin, e.g. in cells, cell exudates or body fluids.

Therapeutic Administration of Recombinant Soluble Type II IL-1R

The present invention provides methods of using therapeutic compositions comprising an effective amount of soluble type II IL-1R proteins and a suitable diluent and carrier, and methods for suppressing IL-1-dependent immune responses in humans comprising administering an effective amount of soluble type II IL-1R protein.

For therapeutic use, purified soluble type II IL-1R protein is administered to a patient, preferably a human, for treatment in a manner appropriate to the indication. Thus, for example, soluble type II IL-1R protein compositions can be administered by bolus injection, continuous infusion, sustained release from implants, or other suitable technique. Typically, a soluble type II IL-1R therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the type II IL-1R with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials; generally, shuIL-1R dosages of from about 1 ng/kg/day to about 10 mg/kg/day, and more preferably from about 500 µg/kg/day to about 5 mg/kg/day, are expected to induce a biological effect.

Because IL-1R-I and type II IL-1R proteins both bind to IL-1, soluble type II IL-1R proteins are expected to have similar, if not identical, therapeutic activities. For example, soluble human type II IL-1R can be administered, for example, for the purpose of suppressing immune responses in a human. A variety of diseases or conditions are caused by an immune response to alloantigen, including allograft rejection and graft-versus-host reaction. In alloantigen-induced immune responses, shuIL-1R suppresses lymphoproliferation and inflammation which result upon activation of T cells. shuIl1-1R can therefore be used to effectively suppress alloantigen-induced immune responses in the clinical treatment of, for example, rejection of allografts (such as skin, kidney, and heart transplants), and graft-versus-host reactions in patients who have received bone marrow transplants.

Soluble human type II IL-1R can also be used in clinical treatment of autoimmune dysfunctions, such as rheumatoid arthritis, diabetes and multiple sclerosis, which are dependent upon the activation of T cells against antigens not recognized as being indigenous to the host.

The following examples are offered by way of illustration, and not by way of limitation.

EXAMPLES

Example 1

Isolation of cDNA Encoding Human Type II IL-1R by Direct Expression of Active Protein in CV-1/EBNA-1 Cells A. Radiolabeling of rIL-1β. Recombinant human IL-1β was prepared by expression in *E. coli* and purification to homogeneity as described by Kronheim et al. (*Bio/Technology* 4:1078, 1986). The IL-1β was labeled with di-iodo ($^{125}$I) Bolton-Hunter reagent (New England Nuclear, Glenolden, Pa.). Ten micrograms (0.57 nmol) of protein in 10 µL of phosphate (0.015 mol/L)-buffered saline (PBS; 0.15 mol/L), pH 7.2, was mixed with 10 uL of sodium borate (0.1 mol/L)-buffered saline (0.15 mol/L), pH 8.5, and reacted with 1 mCi (0.23 nmol) of Bolton-Hunter reagent according to the manufacturer's instructions for 12 hours at 8° C. Subsequently, 30 uL of 2% gelatin and 5 uL of 1 mol/L glycine ethyl ester were added, and the protein was separated from unreacted Bolton-Hunter reagent on a 1 mL bed volume Biogel™ P6 column (Bio-Rad Laboratoreis, Richmond, Calif.). Routinely, 50% to 60% incorporation of label was observed. Radioiodination yielded specific activities in the range of $1 \times 10^{15}$ to $5 \times 10^{15}$ cpm/mmol-1 (0.4 to 2 atoms I per molecule protein), and sodium dodecyl sulfate-polyacrylamide gel electrophoresis (SDS-PAGE) revealed a single labeled polypeptide of 17.5 kD, consistant with previously reported values for IL-1. The labeled protein was greater than 98% TCA precipitable, indicating that the $^{125}$I was covalently bound to protein.

B. Construction and Screening of CB23 cDNA library. A CB23 library was constructed and screened by direct expression of pooled cDNA clones in the monkey kidney cell line CV-1/EBNA-1 (which was derived by transfection of the CV-1 cell line with the gene encoding EBNA-1, as described below) using a mammalian expression vector (pDC406) that includes regulatory sequences from SV40, human immunodeficiency virus (HIV), and Epstein-Barr virus (EBV). The CV-1/EBNA-1 cell line constitutively expresses EBV nuclear antigen-1 driven from the human cytomegalovirus (CMV) immediate-early enhancer/promoter and therefore allows the episomal replication of expression vectors such as pDC406 that contain the EBV origin of replication. The expression vector used was pDC406, a derivative of HAV-EO, described by Dower et al., *J. Immunol.* 142:4314, 1989), which is in turn a derivative of pDC201 and allows high level expression in the CV-1/EBNA-1 cell line. pDC406 differs from HAV-EO (Dower et al., supra) by the deletion of the intron present in the adenovirus 2 tripartite leader sequence in HAV-EO (see description of pDC303 below).

The CB23 cDNA library was constructed by reverse transcription of poly(A)$^+$ mRNA isolated from total RNA extracted from the human B cell lymphoblastoid line CB23 (Benjamin & Dower, *Blood* 75:2017, 1990) substantially as described by Ausubel et al., eds., *Current Protocols in Molecular Biology*, Vol. 1, 1987. The CB23 cell line is an EBV-transforned cord blood (CB) lymphocyte cell line, which was derived by using the methods described by Benjamin et al., *Proc. Natl. Acad. Sci. USA* 81:3547, 1984. Poly(A)$^+$ mRNA was isolated by oligo dT cellulose chromatography and double-stranded cDNA was made substantially as described by Gubler and Hoffman, *Gene* 25:263, 1983. Briefly, the poly(A)$^+$ mRNA was converted to an RNA-cDNA hybrid with reverse transcriptase using random hexanucleotides as a primer. The RNA-cDNA hybrid was then converted into double-stranded cDNA using RNAase H in combination with DNA polymerase I. The resulting double stranded cDNA was blunt-ended with T4 DNA polymerase. The following two unkinased oligonucleotides were annealed and blunt end ligated with DNA ligase to the ends of the resulting blunt-ended cDNA as described by Haymerle, et al., *Nucleaic Acids Research*, 14: 8615, 1986.

```
SEQ ID NO:3 5'- TCG ACT GGA ACG AGA CGA CCT GCT -3'
SEQ ID NO:4 3'-     GA CCT TGC TCT GCT GGA CGA -5'
                <SalI>
```

In this case only the 24-mer oligo will ligate onto the cDNA. The non-ligated oligos were removed by gel filtration chromatography at 68° C., leaving 24 nucleotide non-self-complementary overhangs on the cDNA. The same procedure was used to convert the 5' ends of SalI-cut mammalian expression vector pDC406 to 24 nucleotide overhangs complementary to those added to the cDNA. Optimal proportions of adaptored vector and cDNA were ligated in the presence of T4 polynucleotide kinase. Dialyzed ligation mixtures were electroporated into *E. coli* strain DH5α. Approximately $3.9 \times 10^6$ clones were generated and plated in pools of approximately 3,000. A sample of each pool was used to prepare frozen glycerol stocks and a sample was used to obtain a pool of plasmid DNA.

The pooled DNA was then used to transfect a subconfluent layer of monkey CV-1/EBNA-1 cells using DEAE-dextran followed by chloroquine treatment, similar to that described by Luthman et al., *Nucl. Acids Res.* 11:1295 (1983) and McCutchan et al., *J. Natl. Cancer Inst.* 41:351 (1986). CV-1/EBNA-1 cells were derived as follows. The CV-1/EBNA-1 cell line constitutively expresses EBV nuclear antigen-1 driven from the CMV immediate-early enhancer/promoter. The African Green Monkey kidney cell line, CV-1 (ATCC CCL 70, was cotransfected with 5 μg of pSV2gpt (Mulligan & Berg, *Proc. Natl. Acad. Sci. USA* 78:2072, 1981) and 25 ug of pDC303/EBNA-1 using a calcium phosphate coprecipitation technique (Ausubel et al., eds., *Current Protocols in Molecular Biology*, Wiley, New York, 1987). pDC303/EBNA-1 was constructed from pDC302 (Mosley et al., *Cell* 59:335, 1989) in two steps. First, the intron present in the adenovirus tripartite leader sequence was deleted by replacing a PvuII to ScaI fragment spanning the intron with the following synthetic oligonucleotide pair to create plasmid pDC303:

SEQ ID NO:5 5'-CTGTTGGGCTCGCGGTTGAGGA CAAACTCTTCGCGGTCTTTCCAGT-3'

SEQ ID NO:6 3'-GACAACCCGAGCGCCAACT CCTGTTTGAGAAGCGCCAGAAAGGTCA-5'

Second, a HindIII-AhaII restriction fragment encoding Epstein-Barr virus nuclear antigen I (EBNA-1), and consisting essentially of EBV coordinates 107,932 to 109,894 (Baer et al., *Nature* 310:207, 1984), was then inserted into the multiple cloning site of pDC303 to create the plasmid pDC303/EBNA-1. The transfected cells were grown in the presence of hypoxanthine, aminopterin, thymidine, xanthine, and mycophenolic acid according to standard methods (Ausubel et al., supra; Mulligan & Berg, supra) to select for the cells that had stably incorporated the transfected plasmids. The resulting drug resistant colonies were isolated and expanded individually into cell lines for analysis. The cell lines were screened for the expression of functional EBNA-1. One cell line, clone 68, was found to express EBNA-1 using this assay, and was designated CV-1/EBNA-1. CV-1/EBNA-1 cells were deposited with the American Type Culture Collection on Jun. 5, 1990, under the conditions of the Budapest Treaty, and assigned accession number CRL 10478.

In order to transfect the CV-1/EBNA-1 cells with the cDNA library, the cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of $2 \times 10^5$ cells/well in either 6 well dishes (Falcon) or single well chambered slides (Lab-Tek). Both dishes and slides were pretreated with 1 ml human fibronectin (10 ug/ml in PBS) for 30 minutes followed by 1 wash with PBS. Media was removed from the adherent cell layer and replaced with 1.5 ml complete medium containing 66.6 μM chloroquine sulfate. 0.2 mls of DNA solution (2 μg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2.5 to 20 minutes followed by replacement of the solution with fresh complete medium. The cells were grown in culture to permit transient expression of the inserted sequences. These conditions led to an 80% transfection frequency in surviving CV-1/EBNA-1 cells.

After 48 to 72 hours, transfected monolayers of CV-1/EBNA cells were assayed for expression of IL-1 binding proteins by binding radioiodinated IL-1β prepared as described above by slide autoradiography. Transfected CV-1/EBNA-1 cells were washed once with binding medium (RPMI medium 1640 containing 25 mg/ml bovine serum albumin (BSA), 2 mg/ml sodium azide, 20 mM HEPES, pH 7.2, and 50 mg/ml nonfat dry milk (NFDM)) and incubated for 2 hours at 4° C. with 1 ml binding medium+NFDM containing $3 \times 10^{-9}$ M $^{125}$I-IL-1β. After incubation, cells in the chambered slides were washed three times with binding buffer+NFDM, followed by 2 washes with PBS, pH 7.3, to remove unbound $^{125}$I-IL-1β The cells were fixed by incubating for 30 minutes at room temperature in 10% glutaraldehyde in PBS, pH 7.3, washed twice in PBS, and air dried. The slides were dipped in Kodak GTNB-2 photographic emulsion (6× dilution in water) and exposed in the dark for 48 hours to 7 days at 4° C. in a light proof box. The slides were then developed for approximately 5 minutes in Kodak D19 developer (40 g/500 ml water), rinsed in water and fixed in Agfa G433C fixer. The slides were individually examined with a microscope at 25–40× magnification and positive cells expressing type II IL-1R were identified by the presence of autoradiographic silver grains against a light background.

Cells in the 6 well plates were washed once with binding buffer+NFDM followed by 3 washings with PBS, pH 7.3, to remove unbound $^{125}$I-IL-1β. The bound cells were then trypsinized to remove them from the plate and bound $^{125}$I-IL-1β were counted on a beta counter.

Using the slide autoradiography approach, approximately 250,000 cDNAs were screened in pools of approximately 3,000 cDNAs until assay of one transfectant pool showed multiple cells clearly positive for IL-1β binding. This pool was then partitioned into pools of 500 and again screened by slide autoradiography and a positive pool was identified. This pool was further partitioned into pools of 75, plated in 6-well plates and screened by plate binding assays analyzed by quantitation of bound $^{125}$I-IL-1β. The cells were scraped off the plates and counted to determine which pool of 75 was positive. Individual colonies from this pool of 75 were screened until a single clone (clone 75) was identified which directed synthesis of a surface protein with detectable IL-1β binding activity. This clone was isolated, and its insert was sequenced to determine the sequence of the human type II IL-1R cDNA clone 75. The pDC406 cloning vector containing the human type II IL-1R cDNA clone 75, designated pHuIL-1R-II 75, was deposited with the American Type Culture Collection, Rockville, Md., USA (ATCC) on Jun. 5, 1990 under accession number 68337. The Sequence Listing setting forth the nucleotide (SEQ ID No:1) and predicted amino acid sequences of clone 75 (SEQ ID No:1 and SEQ ID NO:2) and associated information appears at the end of the specification immediately prior to the claims.

Example 2

Construction and Expression of cDNAs Encoding Human Soluble Type II IL-1R

A cDNA encoding a soluble human type II IL-1R (having the sequence of amino acids −13–333 of SEQ ID NO:1) was constructed by polymerase chain reaction (PCR) amplification using the full length type II IL-1R cDNA clone 75 (SEQ ID NO:1) in the vector pDC406 as a template. The following 5' oligonucleotide primer (SEQ ID NO:7) and 3' oligonucleotide primer (SEQ ID NO:8) were first constructed:

```
SEQ ID NO:7 5'-GCGTCGACCTAGTGACGCTCATACAAATC-3'
                <SalI>

SEQ ID NO:8 5'-GCGCGGCCGCTCAGGAGGAGGCTTCCTTGACTG-3'
               <-NotI->End\1191              \1172
```

The 5' primer corresponds to nucleotides 31–51 from the untranslated region of human type II IL-1R clone 75 (SEQ ID NO:1) with a 5' add-on of a SalI restriction site; this nucleotide sequence is capable of annealing to the (−) strand complementary to nucleotides 31–51 of human clone 75. The 3' primer is complementary to nucleotides 1191–1172 (which includes anti-sense nucleotides encoding 3 amino acids of human type II IL-1R clone 75 (SEQ ID NO:1) and has a 5' add-on of a NotI restriction site and a stop codon.

The following PCR reagents were added to a 1.5 ml Eppendorf microfuge tube: 10 µl of 10×PCR buffer (500 mM KCl, 100 mM Tris-HCl, pH 8.3 at 25° C., 15 mM MgCl$_2$, and 1 mg/ml gelatin) (Perkin-Elmer Cetus, Norwalk, Conn.), 10 µl of a 2 mM solution containing each dNTP (2 mM dATP, 2 mM dCTP, 2 mM dGTP and 2 mM dTTP), 2.5 units (0.5 µl of standard 5000 units/ml solution) of Taq DNA polymerase (Perkin-Elmer Cetus), 50 ng of template DNA and 5 µl of a 20 µM solution of each of the above oligonucleotide primers and 74.5 µl water to a final volume of 100 µl. The final mixture was then overlaid with 100 µl parafin oil. PCR was carried out using a DNA thermal cycler (Ericomp, San Diego, Calif.) by initially denaturing the template at 94° for 90 seconds, reannealing at 55° for 75 seconds and extending the cDNA at 72° for 150 seconds. PCR was carried out for an additional 20 cycles of amplification using a step program (denaturation at 94°, 25 sec; annealing at 55°, 45 sec; extension at 72°, 150 sec.), followed by a 5 minute extension at 72°.

The sample was removed from the parafin oil and DNA extracted by phenol-chloroform extraction and spun column chromatography over G-50 (Boehringer Mannheim). A 10 µl aliquot of the extracted DNA was separated by electrophoresis on 1% SeaKem™ agarose (FMC BioProducts, Rockland, Me.) and stained with ethidium bromide to confirm that the DNA fragment size was consistent with the predicted product.

20 µl of the PCR-amplified cDNA products were then digested with SalI and NotI restriction enzymes using standard procedures. The SalI/NotI restriction fragment was then separated on a 1.2% Seaplaque™ low gelling temperature (LGT) agarose, and the band representing the fragment was isolated. The fragment was ligated into the pDC406 vector by a standard "in gel" ligation method, and the vector was transfected into CV1-EBNA cells and expressed as described above in Example 1.

Example 3

Isolation of cDNAs Encoding Murine Type II IL-1R

Murine type II IL-1R cDNAs were isolated from a cDNA library made from the murine pre-B cell line 70Z/3 (ATCC TIB 158), by cross species hybridization with a human Type II IL-1R probe. A cDNA library was constructed in a λ phage vector using λgt10 arms and packaged in vitro (Gigapack®, Stratagene, San Diego) according to the manufacturer's instructions. A double-stranded human Type II IL-1R probe was produced by excising an approximately 1.35 kb SalI restriction fragment of the human type II IL-1R clone 75 and $^{32}$P-labelling the cDNA using random primers (Boehringer-Mannheim). The murine cDNA library was amplified once and a total of 5×10$^5$ plaques were screened with the human probe in 35% formamide (5×SSC, 42° C.). Several murine type II IL-1R cDNA clones (including clone λ2) were isolated; however, none of the clones appeared to be full-length. Nucleotide sequence information obtained from the partial clones was used to clone a full-length murine type II IL-1R cDNA as follows.

A full-length cDNA clone encoding murine type II IL-1R was isolated by the method of Rapid Amplification of cDNA Ends (RACE) described by Frohman et al., *Proc. Nati. Acad. Sci. USA* 85:8998, 1988, using RNA from the murine pre-B cell line 70Z3. Briefly, the RACE method uses PCR to amplify copies of a region of cDNA between a known point in the cDNA transcript (determined from nucleotide sequence obtained as described above) and the 3' end. An adaptor-primer having a sequence containing 17 dT base pairs and an adaptor sequence containing three endonuclease recognition sites (to place convenient restriction sites at the 3' end of the cDNA) is used to reverse transcribe a population of mRNA and produce (−) strand cDNA. A primer complementary to a known stretch of sequence in the 5' untranslated region of the murine type II IL-1R clone 2 cDNA, described above, and oriented in the 3' direction is annealed with the (−) strand cDNA and extended to generate a complementary (+) strand cDNA. The resulting double-strand cDNA is amplified by PCR using primers that anneal to the natural 5'-end and synthetic 3'-end poly(A) tail. Details of the RACE procedure are as follows.

The following PCR oligonucleotide primers (d(T)$_{17}$ adaptor-primer, 5' amplification primer and 3' amplificaton primer, respectively) were first constructed:

```
SEQ ID NO:9   5'-CTGCAGGCGGCCGCGGATCC(T)17-3'
                 <PstI><-NotI-><BamHI>

SEQ ID NO:10  5'-GCGTCGACGGCAAGAAGCAGCAAGGTAC-3'
                 <SalI>\15                \34

SEQ ID NO:11  5'-CTGCAGGCGGCCGCGGATCC-3'
                 <PstI><-NotI-><BamHI>
```

Briefly, the d(T)$_{17}$ adapter-primer (SEQ ID NO:9) contains nucleotide sequence anneals to the poly(A)+ region of a population mRNA transcripts and is used to generated (−) strand cDNA reverse transcripts from mRNA; it also contains endonuclease restriction sites for PstI, NotI and BamHI to be introduced into the DNA being amplified by PCR. The 5' amplification primer (SEQ ID NO:10) corresponds to nucleotides 15–34 from the 5' untranslated region of murine type II IL-1R clone λ2 with a 5' add-on of a SalI restriction site; this nucleotide sequence anneals to the (−) strand cDNA generated by reverse transcription with the d(T)$_{17}$ adaptor-primer and is extended to generate (+) strand cDNA. The 3' primer (SEQ ID NO:11) anneals to the (+) strand DNA having the above endonuclease restriction sites and is extended to generate a double-stranded full-length cDNA encoding murine type at II IL-1R, which can then be amplified by a standard PCR reaction. Details of the PCR procedure are as follows.

Poly(A)$^+$ mRNA was isolated by oligo dT cellulose chromatography from total RNA extracted from 70Z/3 cells using standard methods described by Maniatis et al., *Molecular Cloning: A Laboratory Manual* (Cold Spring Harbor Lab., Cold Spring Harbor, N.Y., 1982) and reverse transcribed as follows. Approximately 1 μg of poly(A)$^+$ mRNA in 16.5 μl of water was heated at 68° C. for 3 minutes and then quenched on ice, and added to 2 μl of 10× RTC buffer (500 mM Tris-HCl, pH 8.7 at 22° C., 60 mM MgCl2, 400 mM KCl, 10 mM DTT, each dNTP at 10 mM), 10 units of RNasin (Promega Biotech), 0.5 μg of d(T)$_{17}$-adapter primer and 10 units of AMV reverse transcriptase (Life Sciences) in a total volume of 20 μl, and incubated for a period of 2 hours at 42° C. to reverse transcribe the mRNA and synthesize a pool of cDNA. The reaction mixture was diluted to 1 ml with TE buffer (10 mM Tris-HCl, pH 7.5, 1 mM EDTA) and stored at 4° C. overnight.

Approximately 1 or 5 μl of the cDNA pool was combined with 5 μl of a 20 μM solution of the 5' amplification primer, containing sequence corresponding to the sequence of nucle-oIdes 15–34 of murine type II IL-1R clone λ2, 5 μl of a 20 μM solution of the 3' amplification primer, 10 μl of 10×PCR buffer (500 mM KCl, 100 mM Tris-HCl (pH 8.4, 20° C.), 14 mM MgCl$_2$, and 1 mg/ml gelatin), 4 μl of 5 mM each dNTP (containing 5 mM dATP, 5 mM dCTP, 5 mM dGTP and 5 mM dTTP), 2.5 units (0.5 μl of standard 5000 units/ml solution) of Taq DNA polymerase (Perkin-Elmer Cetus Instruments), diluted to a volume of 100 μl. The final mixture was then overlaid with 100 μl parafin oil. PCR was carried out using a DNA thermal cycler (Perkin-Elmer/Cetus) by initially denaturing the template at 94° for 90 seconds, reannealing at 64° for 75 seconds and extending the cDNA at 72° for 150 seconds. PCR was carried out for an additional 25 cycles of amplification using the following step program (denaturation at 94° for 25 sec; annealing at 55° for 45 sec; extension at 72° for 150 sec.), followed by a 7 minute final extension at 72°.

The sample was removed from the parafin oil and DNA extracted by phenol-chloroform extraction and spun column chromatography over G-50 (Boehringer Mannheim). A 10 μl aliquot of the extracted DNA was separated by electrophoresis on 1% SeaKem™ agarose (FMC BioProducts, Rockland, Me.) and stained with ethidium bromide to confirm that the DNA fragment size was consistent with the predicted product. The gel was then blotted and probed with a 5' 610 bp EcoRI fragment of murine type II IL-1R clone λ2 from above to confirm that the band contained DNA encoding murine type II IL-1R.

The PCR-amplified cDNA products were then concentrated by centrifugation in an Eppendorf microfuge at full speed for 20 min., followed by ethanol precipitation in 1/10 volume sodium acetate (3 M) and 2.5 volume ethanol. 30 μl of the concentrate was digested with SalI and NotI restriction enzymes using standard procedures. The SalI/NotI restriction fragment was then separated on a 1.2% LGT agarose gel, and the band representing the fragment was isolated. The restriction fragments were then purified from the agarose using GeneClean™ (Bio-101, La Jolla, Calif.).

The resulting purified restriction fragment was ligated into the pDC406 vector, which was then transfected into CV1-EBNA cells and expressed as described above in Example 1.

The Sequence Listing setting forth the nucleotide (SEQ ID No:12) and predicted amino acid sequences (SEQ ID No:12 and SEQ ID NO:13) and associated information appears at the end of the specification immediately prior to the claims.

Example 4

Construction and Expression of cDNAs Encoding Murine Soluble Type II IL-1R

A cDNA encoding soluble murine type II IL-1R (having the sequence of amino acids-13–345 of SEQ ID NO:12) was constructed by PCR amplification 70Z/3 poly(A)$^+$ mRNA as a template and the following procedure as described for the full length clone encoding murine type II IL-1R. The following PCR oligonucleotide primers (d(T)$_{17}$ adaptor-primer, 5' amplification primer and 3' amplification primer, respectively) were constructed:

```
SEQ ID NO:9   5'-CTGCAGGCGGCCGCGGATCC(T)17-3'
                 <PstI><-NotI-><BamHI>
SEQ ID NO:10  5'-GCGTCGACGGCAAGAAGCAGCAAGGTAC-3'
                 <SalI>\15                  \34
SEQ ID NO:14  5'-GCGCGGCCGCCTAGGAAGAGACTTCTTTGACTGTGG-3'
                 <---NotI--->EndSerSerValGluLysvalThrThr   SEQ ID NO:20
```

The d(T)$_{17}$ adaptor-primer and 5' amplification primer are identical with SEQ ID NO:9 and SEQ ID NO:10, described in Example 5. The 3' end of SEQ ID NO:12 is complementary to nucleotides 1145–1166 of SEQ ID NO:12 and has a 5' add-on of a NotI restriction site and a stop codon.

A pool of cDNA was synthesized from poly(A)$^+$ mRNA using the d(T)$_{17}$ adaptor-primer as described in Example 3. To a 1.5 ml Eppendorf microfuge tube was added approximately 1 μl of the cDNA pool, 5 μl of a 20 μM solution of the 5' amplification primer, 5 μl of a 20 μM solution of the 3' amplification primer, 10 μL of 10× PCR buffer (500 mM KCl, 100 mM Tris-HCl (pH 8.4 at 20° C.), 14 mM MgCl$_2$, and 1 mg/ml gelatin), 4 μl of 5 mM each of dNTP (containing 5 mM dATP, 5 mM dCTP, 5 mM dGTP and 5 mM dTTP), 2.5 units (0.5 μl of standard 5000 units/ml solution) of Taq DNA polymerase (Perkin-Elmer Cetus Instruments), diluted with 75.4 μl water to a volume of 100 μl. The final mixture was then overlaid with 100 μl parafin oil. PCR was carried out using a DNA thermal cycler (Ericomp) by initially denaturing the template at 94° for 90 seconds, reannealing at 55° for 75 seconds and extending the cDNA at 72° for 150 seconds. PCR was carried out for an additional 20 cycles of amplification using the following step program (denaturation at 94° for 25 sec; annealing at 55° for 45 sec; extension at 72° for 150 sec.), followed by a 7 minute final extension at 72°.

The sample was removed from the parafin oil and DNA extracted by phenol-chloroform extraction and spun column chromatography over G-50 (Boehringer Mannheim). A 10 μl aliquot of the extracted DNA was separated by electrophoresis on 1% SeaKem™ agarose (FMC BioProducts, Rockland, Me.) and stained with ethidium bromide to confirm that the DNA fragment size was consistent with the predicted product.

The PCR-amplified cDNA products were then concentrated by centrifugation in an Eppendorf microfuge at full speed for 20 min., followed by ethanol precipitation in 1/10 volume sodium acetate (3 M) and 2.5 volume ethanol. 50 μl was digested with SalI and NotI restriction enzymes using standard procedures. The SalI/NotI restriction fragment was then separated on a 1.2% Seaplaque LGT agarose gel, and the band representing the fragment was isolated. The restriction fragment was then purified from the isolated band using the following freeze/thaw method. The band from the gel was split into two 175 μl fragments and placed into two 1.5 ml Eppendorf microfuge tubes. 500 1μl of isolation buffer (0.15 M NaCl, 10 mM Tris, pH 8.0, 1 mM EDTA) was added to each tube and the tubes heated to 68° C. to melt the gel. The gels were then frozen on dry ice for 10 minutes, thawed at room temperature and centrifuged at 4° C. for 30 minutes. Supernatants were then removed and placed in a new tube, suspended in 2 mL ethanol, and centrifuged at 4° C. for an additional 30 minutes to form a DNA pellet. The DNA pellet was washed with 70% ethanol, centrifuged for 5 minutes, removed from the tube and resuspended in 20 μl TE buffer.

The resulting purified restriction fragments were then ligated into the pDC406 vector. A sample of the ligation was transformed into DH5α and colonies were analyzed to check for correct plasmids. The vector was then transfected into COS-7 cells and expressed as described above in Example 1.

Example 5

Type II IL-1R Binding Studies

The binding inhibition constant of recombinant human type II IL-1R, expressed and purified as described in Example 1 above, was determined by inhibition binding assays in which varying concentrations of a competitor (IL-1β or IL-1α) was incubated with a constant amount of radiolabeled IL-1β or IL-1α and cells expressing the type II IL-1R. The competitor binds to the receptor and prevents the radiolabeled ligand from binding to the receptor. Binding assays were performed by a phthalate oil separation method essentially as describe by Dower et al., *J. Immunol.* 132:751, 1984 and Park et al., *J. Biol. Chem.* 261:4177, 1986. Briefly, CV1/EBNA cells were incubated in six-well plates (Costar, Cambridge, Mass.) at 4° C. for 2 hours with $^{125}$I-IL-1β in 1 ml binding medium (Roswell Park Memorial Institute (RPMI) 1640 medium containing 2% BSA, 20 mM Hepes buffer, and 0.2% sodium azide, pH 7.2). Sodium azide was included to inhibit internalization and degradation of $^{125}$I-IL-1 by cells at 37° C. The plates were incubated on a gyratory shaker for 1 hour at 37° C. Replicate aliquots of the incubation mixture were then transferred to polyethylene centrifuge tubes containing a phthalate oil mixture comprising 1.5 parts dibutylphthalate, to 1 part bis(s-ethylhexyl) phthalate. Control tubes containing a 100× molar excess of unlabeled IL-1β were also included to determine non-specific binding. The cells with bound $^{125}$I-IL-1 were separated from unbound $^{125}$I-IL-1 by centrifugation for 5 minutes at 15,000×g in an Eppendorf Microfuge. The radioactivity associated with the cells was then determined on a gamma counter. This assay (using unlabeled human IL-1β as a competitor to inhibit binding of $^{125}$I-IL-1β to type II IL-1R) indicated that the full length human type II IL-1R exhibits biphasic binding to IL-1β with a $K_{I1}$ of approximately 19±8×10$^9$ and $K_{I2}$ of approximately 0.2±0.002×10$^9$. Using unlabeled human IL-1β to inhibit binding of $^{125}$I-IL-1α to type II IL-1R, the full length human type II IL-1R exhibited biphasic binding to IL-1β with a $K_{I1}$ of approximately 2.0±1×10$^9$ and $K_{I2}$ of approximately 0.013±0.003×10$^9$.

The binding inhibition constant of the soluble human type II IL-1R, expressed and purified as described in Example 2 above, is determined by a inhibition binding assay in which varying concentrations of an IL-1β competitor is incubated with a constant amount of radiolabeled I-IL-1β and CB23 cells (an Epstein Barr virus transformed cord blood B lymphocyte cell line) expressing the type II IL-1R. Binding assays were also performed by a phtahlate oil separation method essentially as describe by Dower et al., *J. Immunol.* 132:751, 1984 and Park et al., *J. Biol. Chem.* 261:4177, 1986. Briefly, COS-7 cells were transfected with the expression vector pDC406 containing a cDNA encoding the soluble human type II IL-1R described above. Supernatants from the COS cells were harvested 3 days after transfection and serially diluted in binding medium (Roswell Park Memorial Institute (RPMI) 1640 medium containing 2% BSA, 20 mM Hepes buffer, and 0.2% sodium azide, pH 7.2) in 6 well plates to a volume of 50 μl/well. The supernatants were incubated with 50 μl of 9×10$^{-10}$ M $^{125}$I-IL-1β plus 2.5×10$^6$ CB23 cells at 8° C. for 2 hours with agitation. Duplicate 60 μl aliquots of the incubation mixture were then transferred to polyethylene centrifuge tubes containing a phthalate oil mixture comprising 1.5 parts dibutylphthalate, to 1 part bis(s-ethylhexyl)phthalate. A negative control tube containing 3×10$^{-6}$ M unlabeled IL-1β was also included to determine non-specific binding (100% inhibition) and a positive control tube containing 50 ml binding medium with only radiolabled IL-1β was included to determine maxium binding. The cells with bound $^{125}$I-IL-1β were separated from unbound $^{125}$-I-IL-1β by centrifugation for 5 minutes at 15,000×g in an Eppendorf Microfuge. Supernatants containing unbound $^{125}$I-IL-1β were discarded and the cells were carefully rinsed with ice-cold binding medium. The cells were then incubated in 1 ml of trypsin-EDTA at 37° C. for 15 minutes and cells were harvested. The radioactivity of the cells was then determined on a gamma counter. This inhibition binding assay (using soluble human type II IL-1R to inhibit binding of IL-1β) indicated that the soluble human type II IL-1R has a $K_I$ of approximately 3.5×10$^9$ M$^{-1}$. Inhibition of IL-1α binding by soluble human type II IL-1R using the same procedure indicated that soluble human type II IL-1R has a $K_I$ of 1.4×10$^8$ M$^{-1}$.

Murine type II IL-1R exhibits biphasic binding to IL-1β with a $K_{I1}$ of 0.8×10$^9$ and a $K_{I2}$ of less then 0.01×10$^9$.

Example 6

Type II IL-1R Affinity Crosslinking Studies

Affinity crosslinking studies were performed essentially as described by Park et al., *Proc. Natl. Acad. Sci. USA* 84:1669, 1987. Recombinant human IL-1α and IL-1β used in the assays were expressed, purified and labeled as described previously (Dower et al., *J. Exp. Med.* 162:501, 1985; Dower et al., *Nature* 324:266, 1986). Recombinant human IL-1 receptor antagonist (IL-1ra) was cloned using the cDNA sequence published by Eisenberg et al., *Nature* 343:341, 1990, expressed by transient transfection in COS cells, and purified by affinity chromatography on a column of soluble human type I IL-1R coupled to affigel, as described by Dower et al., *J. Immunol.* 143:4314, 1989, and eluted at low pH.

Briefly, CV1/EBNA cells ($4 \times 10^7$/ml) expressing recombinant type II IL-1R were incubated with $^{125}$I-IL-1α or $^{125}$I-IL-1β (1 nM) at 4° C. in the presence and absence of 1 μM excess of unlabeled IL-1as a specificity control for 2 hours. The cells were then washed and bis (sulfosuccinimidyl)suberate was added to a final concentration of 0.1 mg/ml. After 30 min. at 25° C., the cells were washed and resuspended in 100 μl of phosphate-buffered saline (PBS)/1% Triton containing 2 mM leupeptin, 2 mM o-phenanthroline, and 2 mM EGTA to prevent proteolysis. Aliquots of the extract supernatants containing equal amounts (CPM) of $^{125}$I-IL-1 and equal volumes of the specificity controls, were analyzed by SDS/PAGE on a 10% gel using standard techniques.

Figure 4A:
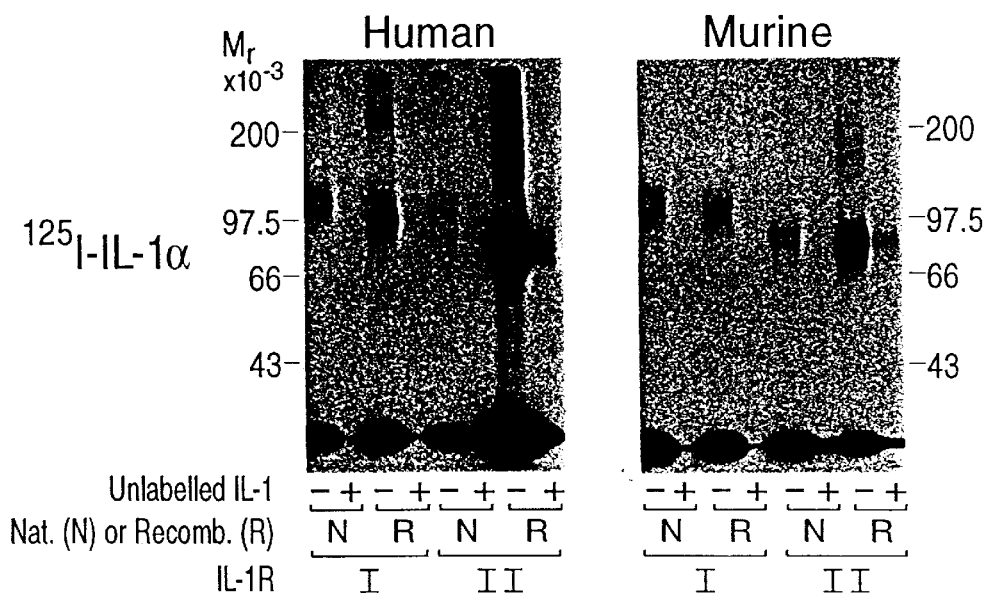
FIG. 4 shows an autoradiograph of an SDS/PAGE gel with crosslinked IL-1 receptors. Cells expressing IL-1 receptors were cross-linked to $^{125}$I-IL-1 in the absence or presence of the cognate unlabeled IL-1 competitor, extracted, electrophoresed and autoradiographed as described in Example 6. Recombinant receptors were expressed transiently in CV1/EBNA cells. The cell lines used for cross-linking to natural receptors were KB (ATCC CCL 1717) (for human type I IL-1R), CB23 (for human type II IL-1R), ELA (ATCC TIB 39) (for murine type I IL-1R), and 70Z/3 (ATCC TIB 158) (for murine type II IL-1R).
Figure 4B:
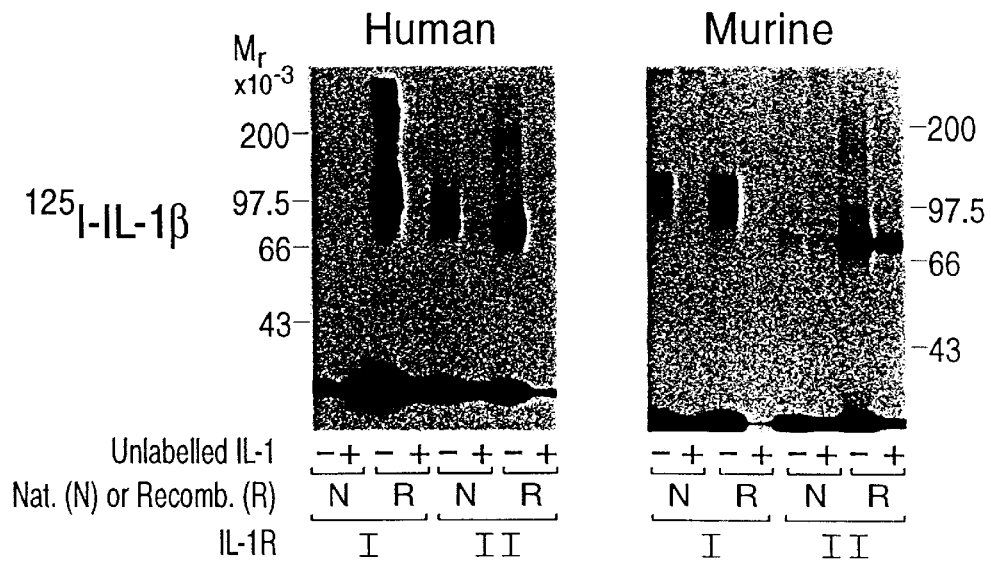

FIG. 4 shows the results of affinity crosslinking studies conducted as described above, using radiolabeled IL-1α and IL-1β, to compare the sizes of the recombinant murine and human type II IL-1 receptor proteins to their natural counterparts, and to natural and recombinant murine and human type I IL-1 receptors. In general, the sizes of the transiently-expressed recombinant receptors are similar to the natural receptors, although the recombinant proteins migrate slightly faster and as slightly broader bands, possibly as a result of differences in glycosylation patter when over-expressed in CV1/EBNA cells. The results also indicate that the type II IL-1 receptors are smaller than the type I IL-1 receptors. One particular combination (natural human type I receptor with IL-1β) failed to yield specific crosslinking products. Since approximately equal amounts of label were loaded into each experimental lane, as indicated by the intensity of the free ligand bands at the bottom of the gels, this combinantion must crosslink relatively poorly.

The lane showing natural human type II IL-1 receptor-bearing cells cross-linked with $^{125}$I-IL-1α reveals a component in the size range ($M_r$=100,000) of complexes with natural and recombinant type I receptors. No such complex can be detected in the lane containing recombinant type II IL-1 receptor, possibly as a result of low level expression of type I IL-1 receptors on the CB23 cells, since these cells contain trace amounts of type I IL-1 receptor mRNA.

Example 7

Preparation of Monoclonal Antibodies to Type II IL-1R

Preparations of purified recombinant type II IL-1R, for example, human type II IL-1R, or transfected COS cells expressing high levels of type II IL-1R are employed to generate monoclonal antibodies against type II IL-1R using conventional techniques, for example, those disclosed in U.S. Pat. No. 4,411,993. Such antibodies are likely to be useful in interfering with IL-1 binding to type II IL-1R, for example, in ameliorating toxic or other undesired effects of IL-1, or as components of diagnostic or research assays for IL-1 or soluble type II IL-1R.

To immunize mice, type II IL-1R immunogen is emulsified in complete Freund's adjuvant and injected in amounts ranging from 10–100 μg subcutaneously and interaperitoneally into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay), or receptor binding inhibition. Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1 or Ag8.653. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with type II IL-1R, for example, by adaptations of the techniques disclosed by Engvall et al., *Immunochem.* 8:871 (1971) and in U.S. Pat. No. 4,703,004. Positive clones are then injected into the peritoneal cavities of syngeneic Balb/c mice to produce ascites containing high concentrations (>1 mg/ml) of anti-type II IL-1R monoclonal antibody, or grown in flasks or roller bottles. The resulting monoclonal antibody can be purified by ammonium sulfate precipitation followed by gel exclusion chromatography, and/or affinity chromatography based on binding of antibody to Protein A of *Staphylococcus aureus* or protein G from Streptococci.

Brief Description of the Sequence Listing

SEQ ID NO:1 and SEQ ID NO:2 show the nucleotide sequence and predicted amino acid sequence of human type II IL-1R. The mature peptide encoded by this sequence is defined by amino acids 1–385. The predicted signal peptide is defined by amino acids -13 through -1. The predicted transmembrane region is defined by amino acids 331–356.

SEQ ID NO:3–SEQ ID NO:6 are various oligonucleotides used to clone the full-length human type I IL-1R.

SEQ ID NO:7 and SEQ ID NO:8 are oligonucleotide primers used to construct a soluble human type II IL-1R by polymerase chain reaction (PCR).

SEQ ID NO:9–SEQ ID NO:11 are oligonucleotide primers used to clone a full-length and soluble murine type II IL-1Rs.

SEQ ID NO:12 and SEQ ID NO:13 show the nucleotide sequence and predicted amino acid sequence of the full-length murine type II IL-1R. The mature peptide encoded by this sequence is defined by amino acids 1–397. The predicted signal peptide is defined by amino acids -13 through -1. The predicted transmembrane region is defined by amino acids 343–368.

SEQ ID NO:14 is an oligonucleotide primer used to construct a soluble murine type II IL-1R.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 1357 base pairs
       (B) TYPE: nucleic acid
       (C) STRANDEDNESS: double
       (D) TOPOLOGY: linear (ii) MOLECULE TYPE: cDNA to mRNA (iii) HYPOTHETICAL: N (iv) ANTI-SENSE: N (vi) ORIGINAL SOURCE:
       (A) ORGANISM: Homo sapiens
       (G) CELL TYPE: Human B cell lymphoblastoid
       (H) CELL LINE: CB23

(vii) IMMEDIATE SOURCE:
       (A) LIBRARY: CB23 cDNA
       (B) CLONE: pHuIL-1RII75

(ix) FEATURE:
       (A) NAME/KEY: CDS
       (B) LOCATION: 154..1350
       (D) OTHER INFORMATION:

(ix) FEATURE:
       (A) NAME/KEY: mat_peptide
       (B) LOCATION: 193..1347
       (D) OTHER INFORMATION:

(ix) FEATURE:
       (A) NAME/KEY: sig_peptide
       (B) LOCATION: 154..192
       (D) OTHER INFORMATION:

(xi) SEQUENCE DESCRIPTION: SEQ ID NO:1:

```
CTGGAAAATA CATTCTGCTA CTCTTAAAAA CTAGTGACGC TCATACAAAT CAACAGAAAG          60

AGCTTCTGAA GGAAGACTTT AAAGCTGCTT CTGCCACGTG CTGCTGGGTC TCAGTCCTCC         120

ACTTCCCGTG TCCTCTGGAA GTTGTCAGGA GCA ATG TTG CGC TTG TAC GTG TTG         174
                                    Met Leu Arg Leu Tyr Val Leu
                                    -13           -10

GTA ATG GGA GTT TCT GCC TTC ACC CTT CAG CCT GCG GCA CAC ACA GGG          222
Val Met Gly Val Ser Ala Phe Thr Leu Gln Pro Ala Ala His Thr Gly
    -5              1               5                   10

GCT GCC AGA AGC TGC CGG TTT CGT GGG AGG CAT TAC AAG CGG GAG TTC          270
Ala Ala Arg Ser Cys Arg Phe Arg Gly Arg His Tyr Lys Arg Glu Phe
15                  20              25

AGG CTG GAA GGG GAG CCT GTA GCC CTG AGG TGC CCC CAG GTG CCC TAC          318
Arg Leu Glu Gly Glu Pro Val Ala Leu Arg Cys Pro Gln Val Pro Tyr
            30              35              40

TGG TTG TGG GCC TCT GTC AGC CCC CGC ATC AAC CTG ACA TGG CAT AAA          366
Trp Leu Trp Ala Ser Val Ser Pro Arg Ile Asn Leu Thr Trp His Lys
45              50              55

AAT GAC TCT GCT AGG ACG GTC CCA GGA GAA GAA GAG ACA CGG ATG TGG          414
Asn Asp Ser Ala Arg Thr Val Pro Gly Glu Glu Glu Thr Arg Met Trp
60              65                  70

GCC CAG GAC GGT GCT CTG TGG CTT CTG CCA GCC TTG CAG GAG GAC TCT          462
Ala Gln Asp Gly Ala Leu Trp Leu Leu Pro Ala Leu Gln Glu Asp Ser
75              80              85                  90
```

```
GGC ACC TAC GTC TGC ACT ACT AGA AAT GCT TCT TAC TGT GAC AAA ATG        510
Gly Thr Tyr Val Cys Thr Thr Arg Asn Ala Ser Tyr Cys Asp Lys Met
 95                 100                 105

TCC ATT GAG CTC AGA GTT TTT GAG AAT ACA GAT GCT TTC CTG CCG TTC        558
Ser Ile Glu Leu Arg Val Phe Glu Asn Thr Asp Ala Phe Leu Pro Phe
        110                 115                 120

ATC TCA TAC CCG CAA ATT TTA ACC TTG TCA ACC TCT GGG GTA TTA GTA        606
Ile Ser Tyr Pro Gln Ile Leu Thr Leu Ser Thr Ser Gly Val Leu Val
125                 130                 135

TGC CCT GAC CTG AGT GAA TTC ACC CGT GAC AAA ACT GAC GTG AAG ATT        654
Cys Pro Asp Leu Ser Glu Phe Thr Arg Asp Lys Thr Asp Val Lys Ile
        140                 145                 150

CAA TGG TAC AAG GAT TCT CTT CTT TTG GAT AAA GAC AAT GAG AAA TTT        702
Gln Trp Tyr Lys Asp Ser Leu Leu Leu Asp Lys Asp Asn Glu Lys Phe
155                 160                 165                 170

CTA AGT GTG AGG GGG ACC ACT CAC TTA CTC GTA CAC GAT GTG GCC CTG        750
Leu Ser Val Arg Gly Thr Thr His Leu Leu Val His Asp Val Ala Leu
175                 180                 185

GAA GAT GCT GGC TAT TAC CGC TGT GTC CTG ACA TTT GCC CAT GAA GGC        798
Glu Asp Ala Gly Tyr Tyr Arg Cys Val Leu Thr Phe Ala His Glu Gly
        190                 195                 200

CAG CAA TAC AAC ATC ACT AGG AGT ATT GAG CTA CGC ATC AAG AAA AAA        846
Gln Gln Tyr Asn Ile Thr Arg Ser Ile Glu Leu Arg Ile Lys Lys Lys
205                 210                 215

AAA GAA GAG ACC ATT CCT GTG ATC ATT TCC CCC CTC AAG ACC ATA TCA        894
Lys Glu Glu Thr Ile Pro Val Ile Ile Ser Pro Leu Lys Thr Ile Ser
        220                 225                 230

GCT TCT CTG GGG TCA AGA CTG ACA ATC CCG TGT AAG GTG TTT CTG GGA        942
Ala Ser Leu Gly Ser Arg Leu Thr Ile Pro Cys Lys Val Phe Leu Gly
235                 240                 245                 250

ACC GGC ACA CCC TTA ACC ACC ATG CTG TGG TGG ACG GCC AAT GAC ACC        990
Thr Gly Thr Pro Leu Thr Thr Met Leu Trp Trp Thr Ala Asn Asp Thr
255                 260                 265

CAC ATA GAG AGC GCC TAC CCG GGA GGC CGC GTG ACC GAG GGG CCA CGC       1038
His Ile Glu Ser Ala Tyr Pro Gly Gly Arg Val Thr Glu Gly Pro Arg
        270                 275                 280

CAG GAA TAT TCA GAA AAT AAT GAG AAC TAC ATT GAA GTG CCA TTG ATT       1086
Gln Glu Tyr Ser Glu Asn Asn Glu Asn Tyr Ile Glu Val Pro Leu Ile
285                 290                 295

TTT GAT CCT GTC ACA AGA GAG GAT TTG CAC ATG GAT TTT AAA TGT GTT       1134
Phe Asp Pro Val Thr Arg Glu Asp Leu His Met Asp Phe Lys Cys Val
        300                 305                 310

GTC CAT AAT ACC CTG AGT TTT CAG ACA CTA CGC ACC ACA GTC AAG GAA       1182
Val His Asn Thr Leu Ser Phe Gln Thr Leu Arg Thr Thr Val Lys Glu
315                 320                 325                 330

GCC TCC TCC ACG TTC TCC TGG GGC ATT GTG CTG GCC CCA CTT TCA CTG       1230
Ala Ser Ser Thr Phe Ser Trp Gly Ile Val Leu Ala Pro Leu Ser Leu
335                 340                 345

GCC TTC TTG GTT TTG GGG GGA ATA TGG ATG CAC AGA CGG TGC AAA CAC       1278
Ala Phe Leu Val Leu Gly Gly Ile Trp Met His Arg Arg Cys Lys His
        350                 355                 360

AGA ACT GGA AAA GCA GAT GGT CTG ACT GTG CTA TGG CCT CAT CAT CAA       1326
Arg Thr Gly Lys Ala Asp Gly Leu Thr Val Leu Trp Pro His His Gln
365                 370                 375

GAC TTT CAA TCC TAT CCC AAG TGA AATAAAT                               1357
Asp Phe Gln Ser Tyr Pro Lys
380                 385
```

(2) INFORMATION FOR SEQ ID NO:2:

(i) SEQUENCE CHARACTERISTICS:
    (A) LENGTH: 398 amino acids
    (B) TYPE: amino acid
    (D) TOPOLOGY: linear (ii) MOLECULE TYPE: protein (xi) SEQUENCE DESCRIPTION: SEQ ID NO:2:

```
Met Leu Arg Leu Tyr Val Leu Val Met Gly Val Ser Ala Phe Thr Leu
-13         -10                 -5                  1

Gln Pro Ala Ala His Thr Gly Ala Ala Arg Ser Cys Arg Phe Arg Gly
        5               10                  15

Arg His Tyr Lys Arg Glu Phe Arg Leu Glu Gly Pro Val Ala Leu
    20              25                  30                  35

Arg Cys Pro Gln Val Pro Tyr Trp Leu Trp Ala Ser Val Ser Pro Arg
    40              45                  50

Ile Asn Leu Thr Trp His Lys Asn Asp Ser Ala Arg Thr Val Pro Gly
    55              60                  65

Glu Glu Thr Arg Met Trp Ala Gln Asp Gly Ala Leu Trp Leu Leu
    70              75                  80

Pro Ala Leu Gln Glu Asp Ser Gly Thr Tyr Val Cys Thr Thr Arg Asn
    85              90                  95

Ala Ser Tyr Cys Asp Lys Met Ser Ile Glu Leu Arg Val Phe Glu Asn
100             105                 110                 115

Thr Asp Ala Phe Leu Pro Phe Ile Ser Tyr Pro Gln Ile Leu Thr Leu
120             125                 130

Ser Thr Ser Gly Val Leu Val Cys Pro Asp Leu Ser Glu Phe Thr Arg
    135             140                 145

Asp Lys Thr Asp Val Lys Ile Gln Trp Tyr Lys Asp Ser Leu Leu Leu
150             155                 160

Asp Lys Asp Asn Glu Lys Phe Leu Ser Val Arg Gly Thr Thr His Leu
    165             170                 175

Leu Val His Asp Val Ala Leu Glu Asp Ala Gly Tyr Tyr Arg Cys Val
180             185                 190                 195

Leu Thr Phe Ala His Glu Gly Gln Gln Tyr Asn Ile Thr Arg Ser Ile
200             205                 210

Glu Leu Arg Ile Lys Lys Lys Glu Glu Thr Ile Pro Val Ile Ile
    215             220                 225

Ser Pro Leu Lys Thr Ile Ser Ala Ser Leu Gly Ser Arg Leu Thr Ile
230             235                 240

Pro Cys Lys Val Phe Leu Gly Thr Gly Thr Pro Leu Thr Thr Met Leu
    245             250                 255

Trp Trp Thr Ala Asn Asp Thr His Ile Glu Ser Ala Tyr Pro Gly Gly
260             265                 270                 275

Arg Val Thr Glu Gly Pro Arg Gln Glu Tyr Ser Glu Asn Asn Glu Asn
280             285                 290

Tyr Ile Glu Val Pro Leu Ile Phe Asp Pro Val Thr Arg Glu Asp Leu
    295             300                 305

His Met Asp Phe Lys Cys Val Val His Asn Thr Leu Ser Phe Gln Thr
310             315                 320

Leu Arg Thr Thr Val Lys Glu Ala Ser Ser Thr Phe Ser Trp Gly Ile
    325             330                 335

Val Leu Ala Pro Leu Ser Leu Ala Phe Leu Val Leu Gly Gly Ile Trp
340             345                 350                 355
```

```
Met His Arg Arg Cys Lys His Arg Thr Gly Lys Ala Asp Gly Leu Thr
        360                 365                 370

Val Leu Trp Pro His His Gln Asp Phe Gln Ser Tyr Pro Lys
        375                 380             385
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:3:

TCGACTGGAA CGAGACGACC TGCT                                        24

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: Y (xi) SEQUENCE DESCRIPTION: SEQ ID NO:4:

GACCTTGCTC TGCTGGACGA                                            20

(2) INFORMATION FOR SEQ ID NO:5:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:5:

CTGTTGGGCT CGCGGTTGAG GACAAACTCT TCGCGGTCTT TCCAGT              46

(2) INFORMATION FOR SEQ ID NO:6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: Y (xi) SEQUENCE DESCRIPTION: SEQ ID NO:6:

```
GACAACCCGA GCGCCAACTC CTGTTTGAGA AGCGCCAGAA AGGTCA                              46
```

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:7:

```
GCGTCGACCT AGTGACGCTC ATACAAATC                                                29
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:8:

```
GCGCGGCCGC TCAGGAGGAG GCTTCCTTGA CTG                                           33
```

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:9:

```
CTGCAGGCGG CCGCGGATCC TTTTTTTTTT TTTTTTT                                       37
```

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:10:

```
GCGTCGACGG CAAGAAGCAG CAAGGTAC                                                 28
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:11:

```
CTGCAGGCGG CCGCGGATCC                                             20
```

(2) INFORMATION FOR SEQ ID NO:12:

(i) SEQUENCE CHARACTERISTICS:
        (A) LENGTH: 1366 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: N (iv) ANTI-SENSE: N (vi) ORIGINAL SOURCE:
        (A) ORGANISM: Mouse
        (H) CELL LINE: 70Z/3

(vii) IMMEDIATE SOURCE:
        (A) LIBRARY: 70Z/3
        (B) CLONE: 12

(ix) FEATURE:
        (A) NAME/KEY: CDS
        (B) LOCATION: 85..1317
        (D) OTHER INFORMATION:

(ix) FEATURE:
        (A) NAME/KEY: mat_peptide
        (B) LOCATION: 124..1314
        (D) OTHER INFORMATION:

(ix) FEATURE:
        (A) NAME/KEY: sig_peptide
        (B) LOCATION: 85..123
        (D) OTHER INFORMATION:

(xi) SEQUENCE DESCRIPTION: SEQ ID NO:12:

```
GTCGACGGCA AGAAGCAGCA AGGTACAAGA ATACACAGCT CCAGGCTCCA AGGGTCCTGT      60

GCGCTCAGGA AGTTGGTGCG GACA ATG TTC ATC TTG CTT GTG TTA GTA ACT       111
                          Met Phe Ile Leu Leu Val Leu Val Thr
                          -13          -10              -5

GGA GTT TCT GCT TTC ACC ACT CCA ACA GTG GTG CAC ACA GGA AAG GTT      159
Gly Val Ser Ala Phe Thr Thr Pro Thr Val Val His Thr Gly Lys Val
 1               5                  10

TCT GAA TCC CCC ATT ACA TCG GAG AAG CCC ACA GTC CAT GGA GAC AAC      207
Ser Glu Ser Pro Ile Thr Ser Glu Lys Pro Thr Val His Gly Asp Asn
 15              20                  25

TGT CAG TTT CGT GGC AGA GAG TTC AAA TCT GAA TTG AGG CTG GAA GGT      255
Cys Gln Phe Arg Gly Arg Glu Phe Lys Ser Glu Leu Arg Leu Glu Gly
             30                  35                  40

GAA CCT GTG GTT CTG AGG TGC CCC TTG GCA CCT CAC TCC GAC ATC TCC      303
Glu Pro Val Val Leu Arg Cys Pro Leu Ala Pro His Ser Asp Ile Ser
```

-continued

```
             45                  50                  55                  60
AGC AGT TCC CAT AGT TTT CTG ACC TGG AGT AAA TTG GAC TCT TCT CAG         351
Ser Ser Ser His Ser Phe Leu Thr Trp Ser Lys Leu Asp Ser Ser Gln
 65                  70                  75

CTG ATC CCA AGA GAT GAG CCA AGG ATG TGG GTG AAG GGT AAC ATA CTC         399
Leu Ile Pro Arg Asp Glu Pro Arg Met Trp Val Lys Gly Asn Ile Leu
         80                  85                  90

TGG ATT CTG CCA GCA GTG CAG CAA GAC TCT GGT ACC TAC ATT TGC ACA         447
Trp Ile Leu Pro Ala Val Gln Gln Asp Ser Gly Thr Tyr Ile Cys Thr
 95                 100                 105

TTC AGA AAC GCA TCC CAC TGT GAG CAA ATG TCT GTG GAA CTC AAG GTC         495
Phe Arg Asn Ala Ser His Cys Glu Gln Met Ser Val Glu Leu Lys Val
        110                 115                 120

TTT AAG AAT ACT GAA GCA TCT CTG CCT CAT GTC TCC TAC TTG CAA ATC         543
Phe Lys Asn Thr Glu Ala Ser Leu Pro His Val Ser Tyr Leu Gln Ile
125                 130                 135                 140

TCA GCT CTC TCC ACC ACC GGG TTA CTA GTG TGC CCT GAC CTG AAA GAA         591
Ser Ala Leu Ser Thr Thr Gly Leu Leu Val Cys Pro Asp Leu Lys Glu
145                 150                 155

TTC ATC TCC AGC AAC GCT GAT GGA AAG ATA CAG TGG TAT AAG GGC GCC         639
Phe Ile Ser Ser Asn Ala Asp Gly Lys Ile Gln Trp Tyr Lys Gly Ala
        160                 165                 170

ATA CTC TTG GAT AAA GGC AAT AAG GAA TTT CTG AGT GCA GGA GAC CCC         687
Ile Leu Leu Asp Lys Gly Asn Lys Glu Phe Leu Ser Ala Gly Asp Pro
175                 180                 185

ACA CGC CTA TTG ATA TCC AAC ACG TCC ATG GAC GAT GCA GGC TAT TAC         735
Thr Arg Leu Leu Ile Ser Asn Thr Ser Met Asp Asp Ala Gly Tyr Tyr
        190                 195                 200

AGA TGT GTT ATG ACA TTT ACC TAC AAT GGC CAG GAA TAC AAC ATC ACT         783
Arg Cys Val Met Thr Phe Thr Tyr Asn Gly Gln Glu Tyr Asn Ile Thr
205                 210                 215                 220

AGG AAT ATT GAA CTC CGG GTC AAA GGA GCA ACC ACG GAA CCC ATC CCT         831
Arg Asn Ile Glu Leu Arg Val Lys Gly Ala Thr Thr Glu Pro Ile Pro
225                 230                 235

GTG ATC ATT TCT CCC CTG GAG ACA ATA CCA GCA TCA TTG GGG TCA AGA         879
Val Ile Ile Ser Pro Leu Glu Thr Ile Pro Ala Ser Leu Gly Ser Arg
        240                 245                 250

CTG ATA GTC CCG TGC AAA GTG TTT CTG GGA ACT GGT ACA TCT TCC AAC         927
Leu Ile Val Pro Cys Lys Val Phe Leu Gly Thr Gly Thr Ser Ser Asn
255                 260                 265

ACC ATT GTG TGG TGG TTG GCT AAC AGC ACG TTT ATC TCG GCT GCT TAC         975
Thr Ile Val Trp Trp Leu Ala Asn Ser Thr Phe Ile Ser Ala Ala Tyr
        270                 275                 280

CCA AGA GGC CGT GTG ACC GAG GGG CTA CAC CAC CAG TAC TCA GAG AAT        1023
Pro Arg Gly Arg Val Thr Glu Gly Leu His His Gln Tyr Ser Glu Asn
285                 290                 295                 300

GAT GAA AAC TAT GTG GAA GTG TCG CTG ATT TTT GAT CCA GTC ACA AGG        1071
Asp Glu Asn Tyr Val Glu Val Ser Leu Ile Phe Asp Pro Val Thr Arg
305                 310                 315

GAG GAT CTG CAT ACA GAT TTT AAA TGT GTT GCC TCG AAT CCA CGG AGT        1119
Glu Asp Leu His Thr Asp Phe Lys Cys Val Ala Ser Asn Pro Arg Ser
        320                 325                 330

TCT CAG TCA CTC CAT ACC ACA GTC AAA GAA GTC TCT TCC ACG TTC TCC        1167
Ser Gln Ser Leu His Thr Thr Val Lys Glu Val Ser Ser Thr Phe Ser
335                 340                 345

TGG AGC ATT GCG CTG GCA CCT CTG TCT CTG ATC ATC TTG GTT GTG GGG        1215
Trp Ser Ile Ala Leu Ala Pro Leu Ser Leu Ile Ile Leu Val Val Gly
        350                 355                 360

GCA ATA TGG ATG CGC AGA CGG TGT AAA CGC AGG GCT GGA AAG ACA TAT        1263
```

```
Ala Ile Trp Met Arg Arg Arg Cys Lys Arg Arg Ala Gly Lys Thr Tyr
365                 370                 375                 380

GGA CTG ACC AAG CTA CGG ACT GAC AAC CAG GAC TTC CCT TCC AGC CCA    1311
Gly Leu Thr Lys Leu Arg Thr Asp Asn Gln Asp Phe Pro Ser Ser Pro
385                 390                 395

AAC TAA ATAAAGGAAA TGAAATAAAA AAAAAAAAAA AAAAAGGATC CGCGGCCGC      1366
Asn
```

(2) INFORMATION FOR SEQ ID NO:13:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:13:

```
Met Phe Ile Leu Leu Val Leu Val Thr Gly Val Ser Ala Phe Thr Thr
-13             -10                 -5                   1

Pro Thr Val Val His Thr Gly Lys Val Ser Glu Ser Pro Ile Thr Ser
         5                  10                  15

Glu Lys Pro Thr Val His Gly Asp Asn Cys Gln Phe Arg Gly Arg Glu
    20                  25                  30                  35

Phe Lys Ser Glu Leu Arg Leu Glu Gly Glu Pro Val Val Leu Arg Cys
    40                  45                  50

Pro Leu Ala Pro His Ser Asp Ile Ser Ser Ser His Ser Phe Leu
        55                  60                  65

Thr Trp Ser Lys Leu Asp Ser Ser Gln Leu Ile Pro Arg Asp Glu Pro
    70                  75                  80

Arg Met Trp Val Lys Gly Asn Ile Leu Trp Ile Leu Pro Ala Val Gln
        85                  90                  95

Gln Asp Ser Gly Thr Tyr Ile Cys Thr Phe Arg Asn Ala Ser His Cys
100                 105                 110                 115

Glu Gln Met Ser Val Glu Leu Lys Val Phe Lys Asn Thr Glu Ala Ser
120                 125                 130

Leu Pro His Val Ser Tyr Leu Gln Ile Ser Ala Leu Ser Thr Thr Gly
    135                 140                 145

Leu Leu Val Cys Pro Asp Leu Lys Glu Phe Ile Ser Ser Asn Ala Asp
150                 155                 160

Gly Lys Ile Gln Trp Tyr Lys Gly Ala Ile Leu Leu Asp Lys Gly Asn
    165                 170                 175

Lys Glu Phe Leu Ser Ala Gly Asp Pro Thr Arg Leu Leu Ile Ser Asn
180                 185                 190                 195

Thr Ser Met Asp Asp Ala Gly Tyr Tyr Arg Cys Val Met Thr Phe Thr
200                 205                 210

Tyr Asn Gly Gln Glu Tyr Asn Ile Thr Arg Asn Ile Glu Leu Arg Val
    215                 220                 225

Lys Gly Ala Thr Thr Glu Pro Ile Pro Val Ile Ile Ser Pro Leu Glu
230                 235                 240

Thr Ile Pro Ala Ser Leu Gly Ser Arg Leu Ile Val Pro Cys Lys Val
    245                 250                 255

Phe Leu Gly Thr Gly Thr Ser Ser Asn Thr Ile Val Trp Trp Leu Ala
260                 265                 270                 275

Asn Ser Thr Phe Ile Ser Ala Ala Tyr Pro Arg Gly Arg Val Thr Glu
        280                 285                 290
```

```
Gly Leu His His Gln Tyr Ser Glu Asn Asp Glu Asn Tyr Val Glu Val
    295                 300                 305

Ser Leu Ile Phe Asp Pro Val Thr Arg Glu Asp Leu His Thr Asp Phe
        310                 315                 320

Lys Cys Val Ala Ser Asn Pro Arg Ser Ser Gln Ser Leu His Thr Thr
        325                 330                 335

Val Lys Glu Val Ser Ser Thr Phe Ser Trp Ser Ile Ala Leu Ala Pro
340                 345                 350                 355

Leu Ser Leu Ile Ile Leu Val Val Gly Ala Ile Trp Met Arg Arg Arg
        360                 365                 370

Cys Lys Arg Arg Ala Gly Lys Thr Tyr Gly Leu Thr Lys Leu Arg Thr
        375                 380                 385

Asp Asn Gln Asp Phe Pro Ser Ser Pro Asn
390                 395
```

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:14:

```
GCGCGGCCGC CTAGGAAGAG ACTTCTTTGA CTGTGG                              36
```

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: FLAG_ peptide (xi) SEQUENCE DESCRIPTION: SEQ ID NO:15:

```
Asp Tyr Lys Asp Asp Asp Asp Lys
 1                 5
```

(2) INFORMATION FOR SEQ ID NO:16:

(i) SEQUENCE CHARACTERISTICS:
        (A) LENGTH: 336 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Human (vii) IMMEDIATE SOURCE:
        (B) CLONE: IL-1R, Type I (xi) SEQUENCE DESCRIPTION: SEQ ID NO:16:

```
Met Lys Val Leu Leu Arg Leu Ile Cys Phe Ile Ala Leu Leu Ile Ser
```

```
1               5                    10                   15
Ser Leu Glu Ala Asp Lys Cys Lys Glu Arg Glu Lys Ile Ile Leu
                20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
            115                 120                 125

Lys Gln Lys Leu Pro Val Ala Gly Asp Gly Gly Leu Val Cys Pro Tyr
        130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
        210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335
```

(2) INFORMATION FOR SEQ ID NO:17:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Murine (vii) IMMEDIATE SOURCE:
        (B) CLONE: IL-1R, Type I (xi) SEQUENCE DESCRIPTION: SEQ ID NO:17:

| | | | | | | | | | | | | | | |
|---|---|---|---|---|---|---|---|---|---|---|---|---|---|---|
| Met | Glu | Asn | Met | Lys | Val | Leu | Leu | Gly | Leu | Ile | Cys | Leu | Met | Val | Pro |
| 1 | | | | 5 | | | | | 10 | | | | | 15 | |

| Leu | Leu | Ser | Leu | Glu | Ile | Asp | Val | Cys | Thr | Glu | Tyr | Pro | Asn | Gln | Ile |
| | | | 20 | | | | | 25 | | | | | 30 | | |

| Val | Leu | Phe | Leu | Ser | Val | Asn | Glu | Ile | Asp | Ile | Arg | Lys | Cys | Pro | Leu |
| | | 35 | | | | | 40 | | | | | 45 | | | |

| Thr | Pro | Asn | Lys | Met | His | Gly | Asp | Thr | Ile | Ile | Trp | Tyr | Lys | Asn | Asp |
| | 50 | | | | | 55 | | | | | 60 | | | | |

| Ser | Lys | Thr | Pro | Ile | Ser | Ala | Asp | Arg | Asp | Ser | Arg | Ile | His | Gln | Gln |
| 65 | | | | | 70 | | | | | 75 | | | | | 80 |

| Asn | Glu | His | Leu | Trp | Phe | Val | Pro | Ala | Lys | Val | Glu | Asp | Ser | Gly | Tyr |
| | | | | 85 | | | | | 90 | | | | | 95 | |

| Tyr | Tyr | Cys | Ile | Val | Arg | Asn | Ser | Thr | Tyr | Cys | Leu | Lys | Thr | Lys | Val |
| | | | 100 | | | | | 105 | | | | | 110 | | |

| Thr | Val | Thr | Val | Leu | Glu | Asn | Asp | Pro | Gly | Leu | Cys | Tyr | Ser | Thr | Gln |
| | | 115 | | | | | 120 | | | | | 125 | | | |

| Ala | Thr | Phe | Pro | Gln | Arg | Leu | His | Ile | Ala | Gly | Asp | Gly | Ser | Leu | Val |
| | 130 | | | | | 135 | | | | | 140 | | | | |

| Cys | Pro | Tyr | Val | Ser | Tyr | Phe | Lys | Asp | Glu | Asn | Asn | Glu | Leu | Pro | Glu |
| 145 | | | | | 150 | | | | | 155 | | | | | 160 |

| Val | Gln | Trp | Tyr | Lys | Asn | Cys | Lys | Pro | Leu | Leu | Leu | Asp | Asn | Val | Ser |
| | | | | 165 | | | | | 170 | | | | | 175 | |

| Phe | Phe | Gly | Val | Lys | Asp | Lys | Leu | Leu | Val | Arg | Asn | Val | Ala | Glu | Glu |
| | | | 180 | | | | | 185 | | | | | 190 | | |

| His | Arg | Gly | Asp | Tyr | Ile | Cys | Arg | Met | Ser | Tyr | Thr | Phe | Arg | Gly | Lys |
| | | 195 | | | | | 200 | | | | | 205 | | | |

| Gln | Tyr | Pro | Val | Thr | Arg | Val | Ile | Gln | Phe | Ile | Thr | Ile | Asp | Glu | Asn |
| | 210 | | | | | 215 | | | | | 220 | | | | |

| Lys | Arg | Asp | Arg | Pro | Val | Ile | Leu | Ser | Pro | Arg | Asn | Glu | Thr | Ile | Glu |
| 225 | | | | | 230 | | | | | 235 | | | | | 240 |

| Ala | Asp | Pro | Gly | Ser | Met | Ile | Gln | Leu | Ile | Cys | Asn | Val | Thr | Gly | Gln |
| | | | | 245 | | | | | 250 | | | | | 255 | |

| Phe | Ser | Asp | Leu | Val | Tyr | Trp | Lys | Trp | Asn | Gly | Ser | Glu | Ile | Glu | Trp |
| | | | 260 | | | | | 265 | | | | | 270 | | |

| Asn | Asp | Pro | Phe | Leu | Ala | Glu | Asp | Tyr | Gln | Phe | Val | Glu | His | Pro | Ser |
| | | 275 | | | | | 280 | | | | | 285 | | | |

| Thr | Lys | Arg | Lys | Tyr | Thr | Leu | Ile | Thr | Thr | Leu | Asn | Ile | Ser | Glu | Val |
| | 290 | | | | | 295 | | | | | 300 | | | | |

| Lys | Ser | Gln | Phe | Tyr | Arg | Tyr | Pro | Phe | Ile | Cys | Val | Val | Lys | Asn | Thr |
| 305 | | | | | 310 | | | | | 315 | | | | | 320 |

| Asn | Ile | Phe | Glu | Ser | Ala | His | Val | Gln | Leu | Ile | Tyr | Pro | Val | Pro | Asp |
| | | | | 325 | | | | | 330 | | | | | 335 | |

| Phe | Lys |

(2) INFORMATION FOR SEQ ID NO:18:

(i) SEQUENCE CHARACTERISTICS:
        (A) LENGTH: 337 amino acids
        (B) TYPE: amino acid
        (C) STRANDEDNESS: single
        (D) TOPOLOGY: linear (ii) MOLECULE TYPE: protein (vi) ORIGINAL SOURCE:

(A) ORGANISM: Murine (vii) IMMEDIATE SOURCE:
          (B) CLONE: MUST2

(xi) SEQUENCE DESCRIPTION: SEQ ID NO:18:

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
                20                  25                  30

Leu Glu Asn Glu Ala Leu Ile Val Arg Cys Pro Gln Arg Gly Arg Ser
            35                  40                  45

Thr Tyr Pro Val Glu Trp Tyr Tyr Ser Asp Thr Asn Glu Ser Ile Pro
        50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
                100                 105                 110

Lys Pro Pro Ser Cys Asn Ile Pro Asp Tyr Leu Met Tyr Ser Thr Val
            115                 120                 125

Arg Gly Ser Asp Lys Asn Phe Lys Ile Thr Cys Pro Thr Ile Asp Leu
        130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
                180                 185                 190

Glu Asn Gly Thr Asn Tyr Ile Val Thr Ala Thr Arg Ser Phe Thr Val
            195                 200                 205

Glu Glu Lys Gly Phe Ser Met Phe Pro Val Ile Thr Asn Pro Pro Tyr
        210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
                260                 265                 270

Glu Glu Glu Gly Arg Asn Glu Ser Ser Asn Asp Met Asp Cys Leu
        275                 280                 285

Thr Ser Val Leu Arg Ile Thr Gly Val Thr Glu Lys Asp Leu Ser Leu
290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ser Lys Glu Cys Pro Ser His Ile
                325                 330                 335

Ala (2) INFORMATION FOR SEQ ID NO:19:

(i) SEQUENCE CHARACTERISTICS:
        (A) LENGTH: 326 amino acids
        (B) TYPE: amino acid
        (C) STRANDEDNESS: single (D) TOPOLOGY: linear (ii) MOLECULE TYPE: protein (vi) ORIGINAL SOURCE:
  (A) ORGANISM: Vaccinia virus (vii) IMMEDIATE SOURCE:
  (B) CLONE: VVB15

(xi) SEQUENCE DESCRIPTION: SEQ ID NO:19:

```
Met Ser Ile Leu Pro Val Ile Phe Leu Ser Ile Phe Phe Tyr Ser Ser
1               5                  10                  15

Phe Val Gln Thr Phe Asn Ala Pro Glu Cys Ile Asp Lys Gly Gln Tyr
            20                  25                  30

Phe Ala Ser Phe Met Glu Leu Glu Asn Glu Pro Val Ile Leu Pro Cys
        35                  40                  45

Pro Gln Ile Asn Thr Leu Ser Ser Gly Tyr Asn Ile Leu Asp Ile Leu
    50                  55                  60

Trp Glu Lys Arg Gly Ala Asp Asn Asp Arg Ile Ile Pro Ile Asp Asn
65                  70                  75                  80

Gly Ser Asn Met Leu Ile Leu Asn Pro Thr Gln Ser Asp Ser Gly Ile
                85                  90                  95

Tyr Ile Cys Ile Thr Thr Asn Glu Thr Tyr Cys Asp Met Met Ser Leu
            100                 105                 110

Asn Leu Thr Ile Val Ser Val Ser Glu Ser Asn Ile Asp Leu Ile Ser
        115                 120                 125

Tyr Pro Gln Ile Val Asn Glu Arg Ser Thr Gly Glu Met Val Cys Pro
    130                 135                 140

Asn Ile Asn Ala Phe Ile Ala Ser Asn Val Asn Ala Asp Ile Ile Trp
145                 150                 155                 160

Ser Gly His Arg Arg Leu Arg Asn Lys Arg Leu Lys Gln Arg Thr Pro
                165                 170                 175

Gly Ile Ile Thr Ile Glu Asp Val Arg Lys Asn Asp Ala Gly Tyr Tyr
            180                 185                 190

Thr Cys Val Leu Glu Tyr Ile Tyr Gly Gly Lys Thr Tyr Asn Val Thr
        195                 200                 205

Arg Ile Val Lys Leu Glu Val Arg Asp Lys Ile Ile Pro Ser Thr Met
    210                 215                 220

Gln Leu Pro Asp Gly Ile Val Thr Ser Ile Gly Ser Asn Leu Thr Ile
225                 230                 235                 240

Ala Cys Arg Val Ser Leu Arg Pro Pro Thr Thr Asp Ala Asp Val Phe
                245                 250                 255

Trp Ile Ser Asn Gly Met Tyr Tyr Glu Glu Asp Asp Gly Asp Gly Asn
            260                 265                 270

Gly Arg Ile Ser Val Ala Asn Lys Ile Tyr Met Thr Asp Lys Arg Arg
        275                 280                 285

Val Ile Thr Ser Arg Leu Asn Ile Asn Pro Val Lys Glu Glu Asp Ala
    290                 295                 300

Thr Thr Phe Thr Cys Met Ala Phe Thr Ile Pro Ser Ile Ser Lys Thr
305                 310                 315                 320

Val Thr Val Ser Ile Thr
                325
```

(2) INFORMATION FOR SEQ ID NO:20:

(i) SEQUENCE CHARACTERISTICS:

```
     (A) LENGTH: 8 amino acids
     (B) TYPE: amino acid
     (D) TOPOLOGY: linear (ii) MOLECULE TYPE: peptide (vii) IMMEDIATE SOURCE:
       (B) CLONE: oligonucleotide primer translate (xi) SEQUENCE DESCRIPTION: SEQ ID NO:20:

Ser Ser Val Glu Lys Val Thr Thr
 1               5
```

We claim:

1. An isolated and purified Type II IL-1 receptor (Type II IL-1R) that binds IL-1, and is encoded by a DNA that hybridizes under moderately stringent conditions with a DNA selected from the group consisting of:
   (a) a DNA encoding a Type II IL-1R having an amino acid sequence as set forth in SEQ ID NO.: 2, having an amino terminus at amino acid 1, and a carboxy terminus selected from the group consisting of an amino acid between amino acids 330 and 385, inclusive, of SEQ ID NO.:2;
   (b) a DNA encoding a Type II IL-1R having an amino acid sequence as set forth in SEQ ID NO:13, having an amino terminus at amino acid 1, and a carboxy terminus selected from the group consisting of an amino acid between amino acids 342 and 397, inclusive, of SEQ ID NO.:13; and
   (c) a DNA encoding a fragment of the polypeptide of (a) or (b), which fragment binds IL-1.

2. The Type II IL-1R according to claim 1, which is a soluble Type II IL-1R.

3. An isolated and purified Type II IL-1 receptor (Type II IL-1R) that binds IL-1, and is encoded by a DNA that hybridizes under stringent conditions (50% formamide, 50° C., 2×SSC) with a DNA selected from the group consisting of:
   (a) a DNA encoding a Type II IL-1R having an amino acid sequence as set forth in SEQ ID NO.: 2, having an amino terminus at amino acid 1, and a carboxy terminus selected from the group consisting of an amino acid between amino acids 330 and 385, inclusive, of SEQ ID NO.:2;
   (b) a DNA encoding a Type II IL-1R having an amino acid sequence as set forth in SEQ ID NO: 13, having an amino terminus at amino acid 1, and a carboxy terminus selected from the group consisting of an amino acid between amino acids 342 and 397, inclusive, of SEQ ID NO.: 13; and
   (c) a DNA encoding a fragment of the polypeptide of (a) or (b), which fragment binds IL-1.

4. The Type II IL-1R according to claim 3, which is a soluble Type II IL-1R.

* * * * *